(12) United States Patent
     Goldberg

(10) Patent No.: US 12,616,571 B2
(45) Date of Patent: May 5, 2026

(54) IMPLANTABLE FRAME AND FRAME RETAINING MECHANISM

(71) Applicant: EDWARDS LIFESCIENCES CORPORATION, Irvine, CA (US)

(72) Inventor: Eran Goldberg, Nesher (IL)

(73) Assignee: Edwards Lifesciences Corporation, Irvine, CA (US)

( * ) Notice: Subject to any disclaimer, the term of this patent is extended or adjusted under 35 U.S.C. 154(b) by 602 days.

(21) Appl. No.: 18/171,258

(22) Filed: Feb. 17, 2023

(65) Prior Publication Data

US 2023/0200987 A1 Jun. 29, 2023

Related U.S. Application Data

(63) Continuation of application No. PCT/US2021/046204, filed on Aug. 17, 2021.

(60) Provisional application No. 63/194,131, filed on May 27, 2021, provisional application No. 63/066,688, filed on Aug. 17, 2020.

(51) Int. Cl.
     *A61F 2/24* (2006.01)

(52) U.S. Cl.
     CPC .......... *A61F 2/2418* (2013.01); *A61F 2/2436* (2013.01); *A61F 2220/0033* (2013.01)

(58) Field of Classification Search
     CPC ....................... A61F 2/2418; A61F 2002/9665
     See application file for complete search history.

(56) References Cited

U.S. PATENT DOCUMENTS

| | | |
|---|---|---|
| 519,297 A | 5/1894 | Bauer |
| 4,035,849 A | 7/1977 | Angell et al. |

| | | |
|---|---|---|
| 4,592,340 A | 6/1986 | Boyles |
| 4,790,843 A | 12/1988 | Carpentier et al. |
| 4,955,895 A | 9/1990 | Sugiyama et al. |
| 4,994,077 A | 2/1991 | Dobben |
| 5,059,177 A | 10/1991 | Towne et al. |
| 5,176,698 A | 1/1993 | Burns et al. |
| 5,192,297 A | 3/1993 | Hull |
| 5,266,073 A | 11/1993 | Wall |

(Continued)

FOREIGN PATENT DOCUMENTS

| | | |
|---|---|---|
| DE | 19532846 A1 | 3/1997 |
| DE | 19907646 A1 | 8/2000 |

(Continued)

OTHER PUBLICATIONS

Walther, et al., "Trans-catheter valve-in-valve implantation: in vitro hydrodynamic performance of the SAPIEN + cloth trans-catheter heart valve in the Carpentier-Edwards Perimount valves," European Journal of Cardio-thoracic Surgery, 40 (2011) 1120-1126, Sep. 23, 2010.

*Primary Examiner* — Brian A Dukert
(74) *Attorney, Agent, or Firm* — Klarquist Sparkman LLP

(57) ABSTRACT

Embodiments of an implantable frame are disclosed. The frame can have a plurality of struts interconnected to each other to form a mesh structure that is radially expandable and compressible. The frame can have a connecting post extending from an end of the frame. The connecting post can have a body portion and a head portion affixed to an end of the body portion. The head portion can have a first edge extending outwardly of the body portion. The first edge can have a substantially flat portion that is substantially perpendicular to the body portion.

21 Claims, 7 Drawing Sheets

(56) References Cited

U.S. PATENT DOCUMENTS

| | | |
|---|---|---|
| 5,325,845 A | 7/1994 | Adair |
| 5,358,496 A | 10/1994 | Ortiz et al. |
| 5,411,552 A | 5/1995 | Andersen et al. |
| 5,554,185 A | 9/1996 | Block et al. |
| 5,591,195 A | 1/1997 | Taheri et al. |
| 5,599,305 A | 2/1997 | Hermann et al. |
| 5,632,760 A | 5/1997 | Sheiban et al. |
| 5,639,274 A | 6/1997 | Fischell et al. |
| 5,728,068 A | 3/1998 | Leone et al. |
| 5,749,890 A | 5/1998 | Shaknovich |
| 5,782,809 A | 7/1998 | Umeno et al. |
| 5,824,044 A | 10/1998 | Quiachon et al. |
| 5,840,081 A | 11/1998 | Andersen et al. |
| 5,908,405 A | 6/1999 | Imran et al. |
| 5,916,147 A | 6/1999 | Boury |
| 5,944,690 A | 8/1999 | Falwell et al. |
| 5,961,536 A | 10/1999 | Mickley et al. |
| 5,968,068 A | 10/1999 | Dehdashtian et al. |
| 6,019,777 A | 2/2000 | Mackenzie |
| 6,027,510 A | 2/2000 | Alt |
| 6,033,381 A | 3/2000 | Kontos |
| 6,143,016 A | 11/2000 | Bleam et al. |
| 6,162,208 A | 12/2000 | Hipps |
| 6,168,614 B1 | 1/2001 | Andersen et al. |
| 6,174,327 B1 | 1/2001 | Mertens et al. |
| 6,217,585 B1 | 4/2001 | Houser et al. |
| 6,235,050 B1 | 5/2001 | Quiachon et al. |
| 6,251,092 B1 | 6/2001 | Qin et al. |
| 6,379,372 B1 | 4/2002 | Dehdashtian et al. |
| 6,383,171 B1 | 5/2002 | Gifford et al. |
| 6,419,696 B1 | 7/2002 | Ortiz et al. |
| 6,425,916 B1 | 7/2002 | Garrison et al. |
| 6,432,134 B1 | 8/2002 | Anson et al. |
| 6,454,799 B1 | 9/2002 | Schreck |
| 6,458,153 B1 | 10/2002 | Bailey et al. |
| 6,461,382 B1 | 10/2002 | Cao |
| 6,471,672 B1 | 10/2002 | Brown et al. |
| 6,500,147 B2 | 12/2002 | Omaleki et al. |
| 6,514,228 B1 | 2/2003 | Hamilton et al. |
| 6,527,979 B2 | 3/2003 | Constantz et al. |
| 6,579,305 B1 | 6/2003 | Lashinski |
| 6,582,462 B1 | 6/2003 | Andersen et al. |
| 6,652,578 B2 | 11/2003 | Bailey et al. |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,764,504 B2 | 7/2004 | Wang et al. |
| 6,767,362 B2 | 7/2004 | Schreck |
| 6,797,002 B2 | 9/2004 | Spence et al. |
| 6,830,584 B1 | 12/2004 | Seguin |
| 6,893,460 B2 | 5/2005 | Spenser et al. |
| 6,908,481 B2 | 6/2005 | Cribier |
| 7,011,094 B2 | 3/2006 | Rapacki et al. |
| 7,018,406 B2 | 3/2006 | Seguin et al. |
| 7,018,408 B2 | 3/2006 | Bailey et al. |
| 7,037,334 B1 | 5/2006 | Hlavka et al. |
| 7,077,861 B2 | 7/2006 | Spence |
| 7,101,395 B2 | 9/2006 | Tremulis et al. |
| 7,125,421 B2 | 10/2006 | Tremulis et al. |
| 7,137,993 B2 | 11/2006 | Acosta et al. |
| 7,276,084 B2 | 10/2007 | Yang et al. |
| 7,318,278 B2 | 1/2008 | Zhang et al. |
| 7,320,702 B2 | 1/2008 | Hammersmark et al. |
| 7,320,704 B2 | 1/2008 | Lashinski et al. |
| 7,374,571 B2 | 5/2008 | Pease et al. |
| 7,393,360 B2 | 7/2008 | Spenser et al. |
| 7,435,257 B2 | 10/2008 | Lashinski et al. |
| 7,445,632 B2 | 11/2008 | McGuckin, Jr. et al. |
| 7,510,575 B2 | 3/2009 | Spenser et al. |
| 7,585,321 B2 | 9/2009 | Cribier |
| 7,594,926 B2 | 9/2009 | Linder et al. |
| 7,597,709 B2 | 10/2009 | Goodin |
| 7,618,446 B2 | 11/2009 | Andersen et al. |
| 7,637,946 B2 | 12/2009 | Solem et al. |
| 7,708,775 B2 | 5/2010 | Rowe et al. |
| 7,737,060 B2 | 6/2010 | Strickler et al. |
| 7,780,723 B2 | 8/2010 | Taylor |
| 7,785,366 B2 | 8/2010 | Maurer et al. |
| 7,951,195 B2 | 5/2011 | Antonsson et al. |
| 7,959,661 B2 | 6/2011 | Hijlkema et al. |
| 8,029,556 B2 | 10/2011 | Rowe |
| 8,142,492 B2 | 3/2012 | Forster et al. |
| 8,167,932 B2 | 5/2012 | Bourang et al. |
| 8,236,049 B2 | 8/2012 | Rowe et al. |
| RE43,882 E | 12/2012 | Hopkins et al. |
| 8,323,335 B2 | 12/2012 | Rowe et al. |
| 8,377,115 B2 | 2/2013 | Thompson |
| 8,398,708 B2 | 3/2013 | Meiri et al. |
| 8,449,605 B2 | 5/2013 | Lichtenstein et al. |
| 8,449,606 B2 | 5/2013 | Eliasen et al. |
| 8,475,523 B2 | 7/2013 | Duffy |
| 8,568,472 B2 | 10/2013 | Marchand et al. |
| 8,657,872 B2 | 2/2014 | Seguin |
| 8,663,322 B2 | 3/2014 | Keranen |
| 8,672,998 B2 | 3/2014 | Lichtenstein et al. |
| 8,685,086 B2 | 4/2014 | Navia et al. |
| 8,734,507 B2 | 5/2014 | Keranen |
| 8,801,776 B2 | 8/2014 | House et al. |
| 9,061,119 B2 | 6/2015 | Le et al. |
| 9,078,747 B2 | 7/2015 | Conklin |
| 9,095,434 B2 | 8/2015 | Rowe |
| 9,119,716 B2 | 9/2015 | Lee et al. |
| 9,119,718 B2 | 9/2015 | Keranen |
| 9,192,471 B2 | 11/2015 | Bolling |
| 9,237,886 B2 | 1/2016 | Seguin et al. |
| 9,314,335 B2 | 4/2016 | Konno |
| 9,364,326 B2 | 6/2016 | Yaron |
| 9,463,268 B2 | 10/2016 | Spence |
| 9,474,599 B2 | 10/2016 | Keranen |
| 9,526,572 B2 | 12/2016 | Kunis |
| 9,597,205 B2 | 3/2017 | Tuval |
| 9,622,863 B2 | 4/2017 | Karapetian et al. |
| 9,795,477 B2 | 10/2017 | Tran et al. |
| 10,932,931 B2 * | 3/2021 | Phillips .................. A61F 2/966 |
| 11,273,038 B2 | 3/2022 | Tang et al. |
| 2001/0002445 A1 | 5/2001 | Vesely |
| 2001/0007082 A1 | 7/2001 | Dusbabek et al. |
| 2002/0032481 A1 | 3/2002 | Gabbay |
| 2002/0058995 A1 | 5/2002 | Stevens |
| 2002/0107535 A1 | 8/2002 | Wei et al. |
| 2002/0151970 A1 | 10/2002 | Garrison et al. |
| 2002/0165461 A1 | 11/2002 | Hayzelden et al. |
| 2003/0040792 A1 | 2/2003 | Gabbay |
| 2003/0050694 A1 | 3/2003 | Yang et al. |
| 2003/0120341 A1 | 6/2003 | Shennib et al. |
| 2003/0225420 A1 | 12/2003 | Wardle |
| 2004/0093061 A1 | 5/2004 | Acosta et al. |
| 2004/0111006 A1 | 6/2004 | Alferness et al. |
| 2004/0133263 A1 | 7/2004 | Dusbabek et al. |
| 2004/0143197 A1 | 7/2004 | Soukup et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0080474 A1 | 4/2005 | Andreas et al. |
| 2005/0096736 A1 | 5/2005 | Osse et al. |
| 2005/0119682 A1 | 6/2005 | Nguyen et al. |
| 2005/0119735 A1 | 6/2005 | Spence et al. |
| 2005/0137689 A1 | 6/2005 | Salahieh et al. |
| 2005/0137691 A1 | 6/2005 | Salahieh et al. |
| 2005/0149160 A1 | 7/2005 | McFerran |
| 2005/0182486 A1 | 8/2005 | Gabbay |
| 2005/0203614 A1 | 9/2005 | Forster et al. |
| 2005/0203617 A1 | 9/2005 | Forster et al. |
| 2005/0245894 A1 | 11/2005 | Zadno-Azizi |
| 2006/0025857 A1 | 2/2006 | Bergheim et al. |
| 2006/0195134 A1 | 8/2006 | Crittenden |
| 2006/0271172 A1 | 11/2006 | Tehrani |
| 2006/0282150 A1 | 12/2006 | Olson et al. |
| 2007/0005131 A1 | 1/2007 | Taylor |
| 2007/0073389 A1 | 3/2007 | Bolduc et al. |
| 2007/0088431 A1 | 4/2007 | Bourang et al. |
| 2007/0100356 A1 | 5/2007 | Lucatero et al. |
| 2007/0112422 A1 | 5/2007 | Dehdashtian |
| 2007/0203575 A1 | 8/2007 | Forster et al. |

(56)                    References Cited

U.S. PATENT DOCUMENTS

| | | |
|---|---|---|
| 2007/0219612 A1 | 9/2007 | Andreas et al. |
| 2007/0239254 A1 | 10/2007 | Chia et al. |
| 2007/0244546 A1 | 10/2007 | Francis |
| 2007/0265700 A1 | 11/2007 | Eliasen et al. |
| 2007/0293808 A1 | 12/2007 | Williams et al. |
| 2008/0033542 A1 | 2/2008 | Antonsson et al. |
| 2008/0065011 A1 | 3/2008 | Marchand et al. |
| 2008/0077235 A1 | 3/2008 | Kirson |
| 2008/0103520 A1 | 5/2008 | Selkee |
| 2008/0125853 A1 | 5/2008 | Bailey et al. |
| 2008/0208330 A1 | 8/2008 | Keranen |
| 2008/0294230 A1 | 11/2008 | Parker |
| 2009/0024428 A1 | 1/2009 | Hudock, Jr. |
| 2009/0069889 A1 | 3/2009 | Suri et al. |
| 2009/0138079 A1 | 5/2009 | Tuval et al. |
| 2009/0157175 A1 | 6/2009 | Benichou |
| 2009/0192585 A1 | 7/2009 | Bloom et al. |
| 2009/0192601 A1 | 7/2009 | Rafiee et al. |
| 2009/0228093 A1 | 9/2009 | Taylor et al. |
| 2009/0276040 A1 | 11/2009 | Rowe et al. |
| 2009/0281619 A1 | 11/2009 | Le et al. |
| 2009/0299456 A1 | 12/2009 | Melsheimer |
| 2009/0319037 A1 | 12/2009 | Rowe et al. |
| 2010/0030318 A1 | 2/2010 | Berra |
| 2010/0036472 A1 | 2/2010 | Papp |
| 2010/0036473 A1 | 2/2010 | Roth |
| 2010/0036484 A1 | 2/2010 | Hariton et al. |
| 2010/0049313 A1 | 2/2010 | Alon et al. |
| 2010/0076402 A1 | 3/2010 | Mazzone et al. |
| 2010/0076541 A1 | 3/2010 | Kumoyama |
| 2010/0082089 A1 | 4/2010 | Quadri et al. |
| 2010/0094394 A1 | 4/2010 | Beach et al. |
| 2010/0121425 A1 | 5/2010 | Shimada |
| 2010/0145431 A1 | 6/2010 | Wu et al. |
| 2010/0145440 A1 | 6/2010 | Keranen |
| 2010/0161036 A1 | 6/2010 | Pintor et al. |
| 2010/0174363 A1 | 7/2010 | Castro |
| 2010/0198347 A1 | 8/2010 | Zakay et al. |
| 2010/0274344 A1 | 10/2010 | Dusbabek et al. |
| 2010/0312333 A1 | 12/2010 | Navia et al. |
| 2010/0318184 A1 | 12/2010 | Spence |
| 2011/0015729 A1 | 1/2011 | Jimenez et al. |
| 2011/0054596 A1 | 3/2011 | Taylor |
| 2011/0137331 A1 | 6/2011 | Walsh et al. |
| 2011/0160846 A1 | 6/2011 | Bishop et al. |
| 2012/0059458 A1 | 3/2012 | Buchbinder et al. |
| 2012/0123529 A1 | 5/2012 | Levi et al. |
| 2012/0239142 A1 | 9/2012 | Liu et al. |
| 2012/0283820 A1 | 11/2012 | Tseng et al. |
| 2013/0030519 A1 | 1/2013 | Tran et al. |
| 2013/0190865 A1 | 7/2013 | Anderson |
| 2013/0204311 A1 | 8/2013 | Kunis |
| 2013/0317598 A1 | 11/2013 | Rowe et al. |
| 2014/0074299 A1 | 3/2014 | Endou et al. |
| 2014/0081394 A1 | 3/2014 | Keranen et al. |
| 2014/0163669 A1 | 6/2014 | Ben-Zvi et al. |
| 2014/0172070 A1 | 6/2014 | Seguin |
| 2014/0296962 A1 | 10/2014 | Cartledge et al. |
| 2014/0358222 A1 | 12/2014 | Gorman, III et al. |
| 2014/0379074 A1 | 12/2014 | Spence et al. |
| 2015/0025623 A1 | 1/2015 | Granada et al. |
| 2015/0190227 A1 | 7/2015 | Johnson et al. |
| 2015/0230921 A1 | 8/2015 | Chau et al. |
| 2015/0245910 A1 | 9/2015 | Righini et al. |
| 2015/0282931 A1 | 10/2015 | Brunnett et al. |
| 2015/0335428 A1 | 11/2015 | Keranen |
| 2015/0335430 A1 | 11/2015 | Loulmet et al. |
| 2015/0374493 A1 | 12/2015 | Yaron et al. |
| 2016/0015514 A1 | 1/2016 | Lashinski et al. |
| 2016/0074165 A1 | 3/2016 | Spence et al. |

| | | |
|---|---|---|
| 2016/0095705 A1 | 4/2016 | Keranen et al. |
| 2016/0143732 A1 | 5/2016 | Glimsdale |
| 2016/0184095 A1 | 6/2016 | Spence et al. |
| 2016/0199177 A1 | 7/2016 | Spence et al. |
| 2016/0256276 A1 | 9/2016 | Yaron |
| 2016/0346080 A1 | 12/2016 | Righini et al. |
| 2017/0007399 A1 | 1/2017 | Keranen |
| 2017/0007402 A1 | 1/2017 | Zerkowski et al. |
| 2017/0065415 A1 | 3/2017 | Rupp et al. |
| 2017/0217385 A1 | 8/2017 | Rinkleff et al. |
| 2017/0266005 A1 | 9/2017 | McGuckin, Jr. |
| 2017/0273788 A1 | 9/2017 | O'Carroll et al. |
| 2017/0273789 A1 | 9/2017 | Yaron et al. |
| 2017/0281337 A1 | 10/2017 | Campbell |
| 2017/0360426 A1 | 12/2017 | Hacohen et al. |
| 2018/0000580 A1 | 1/2018 | Wallace et al. |
| 2018/0085217 A1 | 3/2018 | Lashinski et al. |
| 2018/0153689 A1 | 6/2018 | Maimon et al. |
| 2018/0206074 A1 | 7/2018 | Tanasa et al. |
| 2018/0289481 A1 | 10/2018 | Dolan |
| 2018/0303606 A1 | 10/2018 | Rothstein et al. |
| 2018/0318073 A1 | 11/2018 | Tseng et al. |
| 2018/0318080 A1 | 11/2018 | Quill et al. |
| 2018/0344456 A1 | 12/2018 | Barash et al. |

FOREIGN PATENT DOCUMENTS

| | | |
|---|---|---|
| EP | 0592410 B1 | 10/1995 |
| EP | 0850607 A1 | 7/1998 |
| EP | 1432369 A1 | 6/2004 |
| EP | 1521550 A2 | 4/2005 |
| EP | 1296618 B1 | 1/2008 |
| EP | 1827314 B1 | 12/2010 |
| EP | 2620125 A1 | 7/2013 |
| EP | 2726018 A2 | 5/2014 |
| EP | 2806829 A2 | 12/2014 |
| FR | 2815844 A1 | 5/2002 |
| WO | 9117720 A1 | 11/1991 |
| WO | 9829057 A1 | 7/1998 |
| WO | 9912483 A1 | 3/1999 |
| WO | 0149213 A2 | 7/2001 |
| WO | 0154625 A1 | 8/2001 |
| WO | 0176510 A2 | 10/2001 |
| WO | 0222054 | 3/2002 |
| WO | 0236048 A1 | 5/2002 |
| WO | 0247575 A2 | 6/2002 |
| WO | 02060352 | 8/2002 |
| WO | 03028558 A2 | 4/2003 |
| WO | 03030776 A2 | 4/2003 |
| WO | 03047468 | 6/2003 |
| WO | 2004019825 A1 | 3/2004 |
| WO | 2005084595 A1 | 9/2005 |
| WO | 2005102015 A2 | 11/2005 |
| WO | 2006011127 A2 | 2/2006 |
| WO | 2006032051 A2 | 3/2006 |
| WO | 2006111391 A1 | 10/2006 |
| WO | 2006138173 A2 | 12/2006 |
| WO | 2007047488 A2 | 4/2007 |
| WO | 2007067942 A1 | 6/2007 |
| WO | 2009155561 A2 | 12/2009 |
| WO | 2010121076 A2 | 10/2010 |
| WO | 2012063228 A1 | 5/2012 |
| WO | 2013110722 A2 | 8/2013 |
| WO | 2013114214 A2 | 8/2013 |
| WO | 2015023579 A1 | 2/2015 |
| WO | 2015023862 A2 | 2/2015 |
| WO | 2015127264 A1 | 8/2015 |
| WO | 2015198125 A1 | 12/2015 |
| WO | 2016038017 A1 | 3/2016 |
| WO | 2016040881 A1 | 3/2016 |
| WO | 2016130820 A1 | 8/2016 |
| WO | 2017103833 A1 | 6/2017 |

* cited by examiner

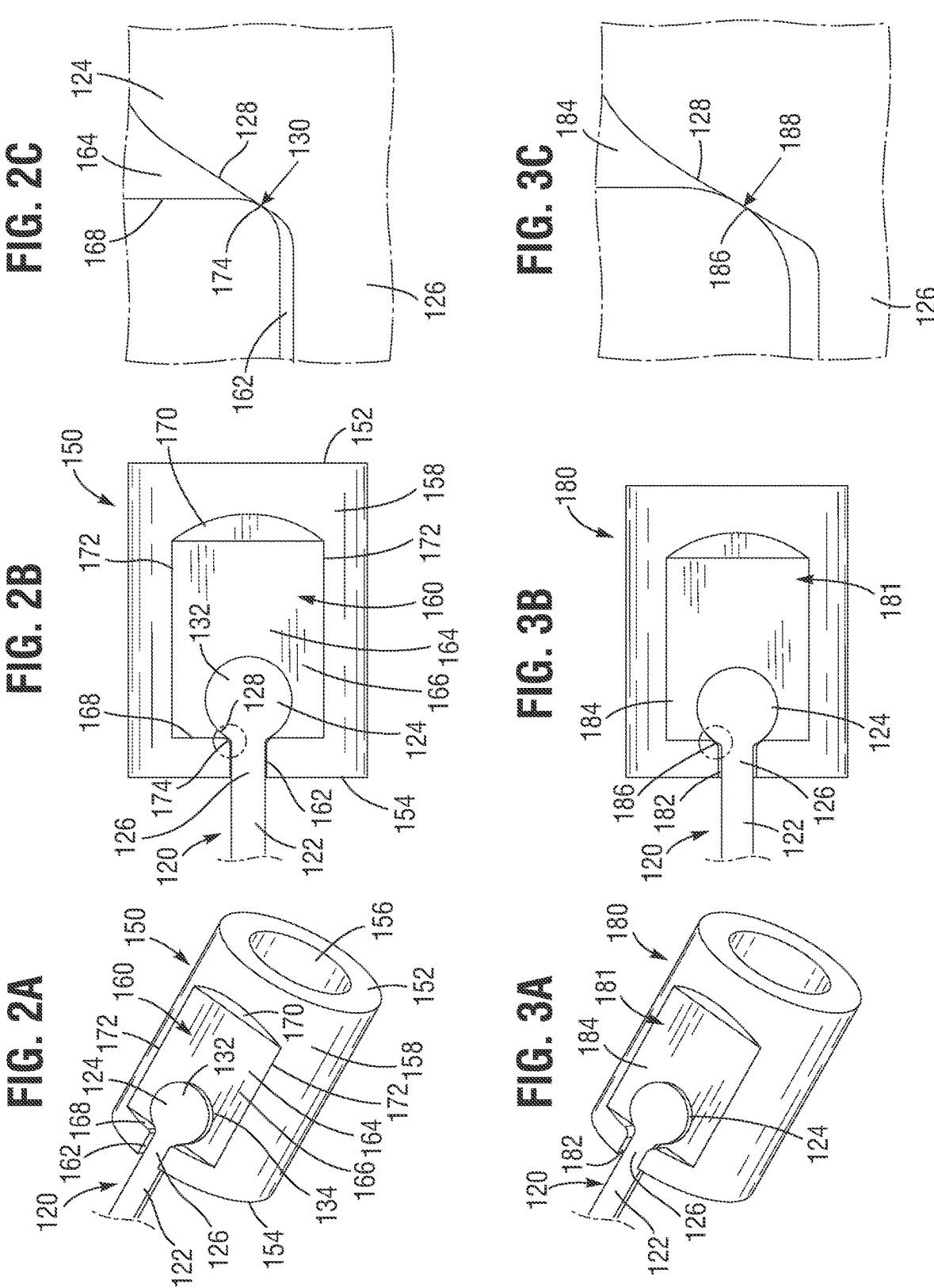

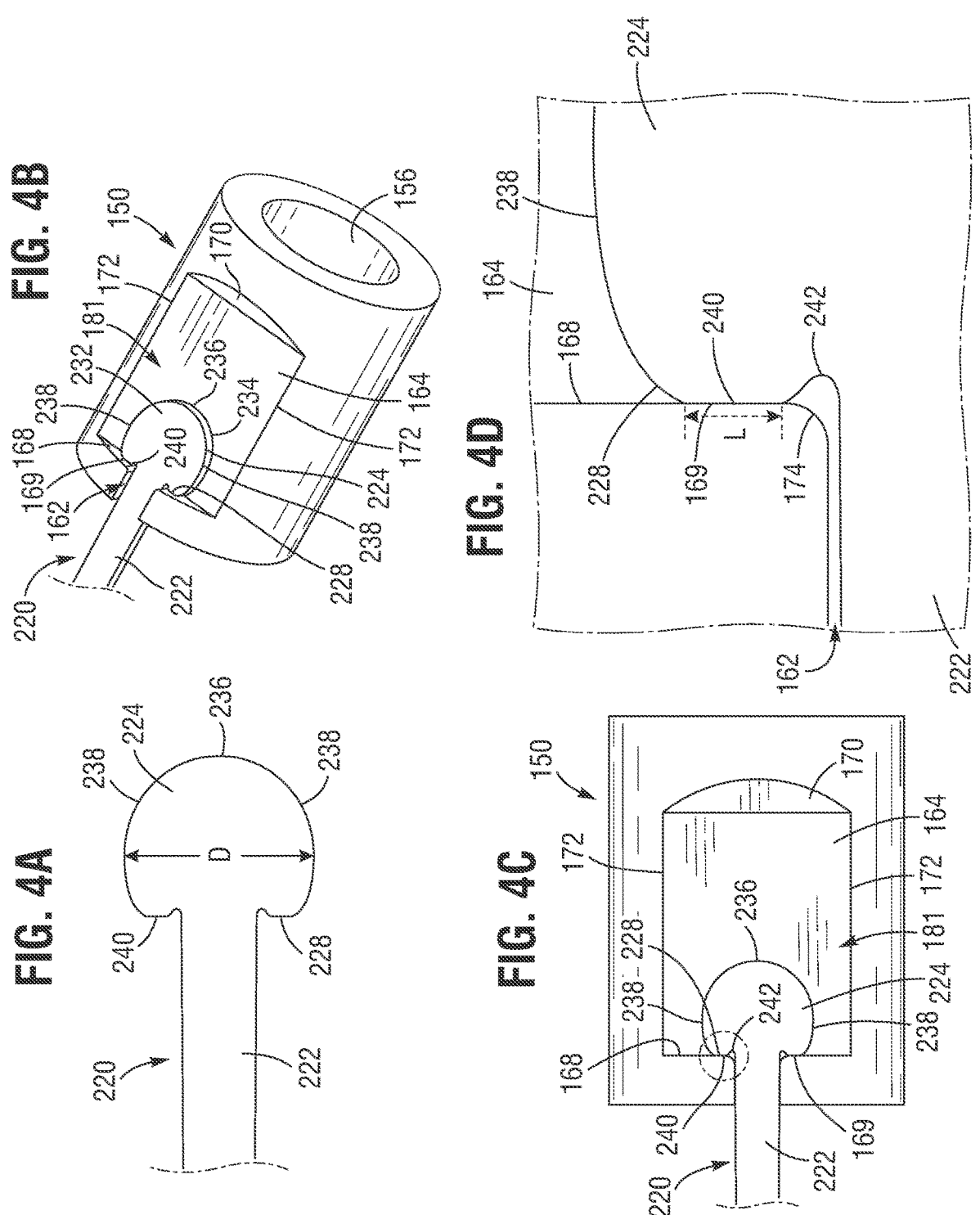

IMPLANTABLE FRAME AND FRAME RETAINING MECHANISM

CROSS-REFERENCE TO RELATED APPLICATIONS

This application is a continuation of PCT Patent Application No. PCT/US2021/046204, filed Aug. 17, 2021, which claims the benefit of both U.S. Provisional Application No. 63/066,688, filed Aug. 17, 2020, and U.S. Provisional Application No. 63/194,131, filed May 27, 2021, each of which is incorporated herein by reference.

FIELD

The present disclosure concerns embodiments of a frame for implantation into body ducts and related frame retaining mechanism for facilitating implantation of the frame, as well as embodiments of a delivery apparatus for transcatheter valve implantation.

BACKGROUND

Prosthetic heart valves can be used to treat cardiac valvular disorders. The native heart valves (the aortic, pulmonary, tricuspid and mitral valves) function to prevent backward flow or regurgitation, while allowing forward flow. These heart valves can be rendered less effective by congenital, inflammatory, infectious conditions, etc. Such conditions can eventually lead to serious cardiovascular compromise or death. For many years, the doctors attempted to treat such disorders with surgical repair or replacement of the valve during open heart surgery.

A transcatheter technique for introducing and implanting a prosthetic heart valve using a catheter in a manner that is less invasive than open heart surgery can reduce complications associated with open heart surgery. In this technique, a prosthetic valve can be mounted in a compressed state on the end portion of a catheter and advanced through a blood vessel of the patient until the valve reaches the implantation site. The valve at the catheter tip can then be expanded to its functional size at the site of the defective native valve, such as by inflating a balloon on which the valve is mounted or, for example, the valve can have a resilient, self-expanding stent or frame that expands the valve to its functional size when it is advanced from a delivery sheath at the distal end of the catheter. Optionally, the valve can have a balloon-expandable, self-expanding, mechanically expandable frame, and/or a frame expandable in multiple or a combination of ways.

Transcatheter heart valves (THVs) may be appropriately sized to be placed inside many native aortic valves. However, with larger native valves, blood vessels (e.g., an enlarged aorta), grafts, etc., aortic transcatheter valves might be too small to secure into the larger implantation or deployment site. In this case, the transcatheter valve may not be large enough to sufficiently expand inside the native valve or other implantation or deployment site. Also, the implantation or deployment site may not provide a good seat for the THV to be secured in place. As one example, aortic insufficiency can be associated with difficulty securely implanting a THV in the aorta and/or aortic valve.

Accordingly, improvements to the THVs and the associated transcatheter delivery apparatus are desirable.

SUMMARY

This summary is meant to provide examples and is not intended to limit the scope of the invention in any way.

Generally, the present disclosure is directed toward methods and apparatuses relating to implanting a stent frame into a target implantation site via a patient's vasculature. As described more fully below, the stent frame can be a part of a prosthetic valve, a part of a docking station or docking device configured to receive a prosthetic valve, part of stent graft or other implantable devices.

Certain embodiments of the disclosure concern an implantable frame. The frame can include a plurality of struts interconnected to each other to form a mesh structure. The mesh structure can be radially expandable and compressible. The frame can also include a connecting post extending from an end of the mesh structure. The connecting post can include a body portion and a head portion affixed to an end of the body portion. The head portion can have a first edge extending outwardly of the body portion. The first edge can include a substantially flat portion that is substantially perpendicular to the body portion.

Certain embodiments of the disclosure also concern an assembly. The assembly can include a radially expandable and compressible frame having a plurality of struts interconnected to each other to form a mesh structure and a connecting post extending from an end of the mesh structure. The assembly can also include a delivery device having a retainer configured to be releasably connected to the connecting post. The connecting post can include body portion and a head portion affixed to an end of the body portion. The head portion can have a first edge extending outwardly of the body portion. The first edge can include a substantially flat portion that is substantially perpendicular to the body portion.

Certain embodiments of the disclosure also concern an assembly including a radially expandable and compressible frame and a delivery catheter configured to deliver the frame to a target implantation site. The frame can include a plurality of struts interconnected to each other to form a mesh structure and a connecting post coupled to the frame. The delivery catheter can include a retainer configured to be releasably connected to the connecting post. The connecting post and the retainer can be configured to form a contacting interface that is substantially perpendicular to an axial axis of the delivery catheter when the connecting post is connected to the retainer.

Certain embodiments of the disclosure also concern a method for deploying a self-expandable frame. The method can include retaining the frame in a compressed state within an outer sheath. A connecting post of the frame can be attached to a retainer retained within the outer sheath such that a substantially flat portion of the connecting post abuts against a substantially flat portion of the retainer. The substantially flat portion of the connecting post and the substantially flat portion of the retainer can be substantially perpendicular to an axial axis of the frame.

In certain embodiments, a system comprises a delivery apparatus, the delivery apparatus comprising a handle portion, a first shaft extending distally from the handle portion, and a nose cone mounted to a distal end portion of the first shaft. The system further comprises a stylet comprising a shaft and an end portion that is wider than a diameter of the shaft, the shaft extending though an opening in an apex of the nose cone and through an axial bore of the nose cone. The system further comprises a spacer disposed around the shaft of the stylet and between the apex of the nose cone and the end portion of the stylet.

In certain embodiments, an assembly comprises a nose cone forming a distal end of a delivery apparatus for a prosthetic medical device, the nose cone comprising a tapered body that narrows to an apex at a distal end of the nose cone and an axial bore extending through a center of the tapered body. The assembly further comprises a stylet comprising a shaft extending through the axial bore of the nose cone and an end portion that is wider than the shaft and disposed outside and distal to the apex of the nose cone. The assembly further comprises a spacer disposed around the shaft of the stylet, distal to the apex, and configured to offset the end portion of the stylet from the apex.

The foregoing and other objects, features, and advantages of the invention will become more apparent from the following detailed description, which proceeds with reference to the accompanying figures.

BRIEF DESCRIPTION OF THE DRAWINGS

FIG. 2A is a perspective view of a connecting post of a frame and a retainer configured to receive the connecting post, according to one embodiment.

FIG. 2B is a top perspective view of the connecting post and the retainer depicted in FIG. 2A.

FIG. 2C is a closeup view of a selected region of the connecting post and the retainer marked in FIG. 2B.

FIG. 3A is a perspective view of a connecting post of a frame and a retainer configured to receive the connecting post, according to another embodiment.

FIG. 3B is a top perspective view of the connecting post and the retainer depicted in FIG. 3A.

FIG. 3C is a closeup view of a selected region of the connecting post and the retainer marked in FIG. 3B.

FIG. 4A is a top perspective view of a connecting post, according to an alternative embodiment.

FIG. 4B is a perspective view of the connecting post depicted in FIG. 4A and a retainer configured to receive the connecting post.

FIG. 4C is a top perspective view of the connecting post and the retainer depicted in FIG. 4B.

FIG. 4D is a closeup view of a selected region of the connecting post and the retainer marked in FIG. 4C.

DETAILED DESCRIPTION

Described herein are examples of implantable stent frames and related delivery apparatus. The stent frames disclosed herein can be implanted within any portion of the circulatory system, such as a blood vessel, aorta, inferior vena cava, superior vena cava, pulmonary artery, aortic valve, pulmonary valve, mitral valve, tricuspid valve, etc. As disclosed herein, the phrase "stent frame" and the words "frame" and "stent" are used interchangeably. The disclosed frames can be, for example, the frame of a prosthetic heart valve, a docking device that receives a prosthetic heart valve, the frame of a stent graft, etc.

Also described herein are assemblies for offsetting an apex of a nose cone of a delivery apparatus from an end portion of a stylet inserted through an axial bore of the nose cone during assembly, packaging, and handling of the delivery apparatus prior to insertion into a patient.

Figures 1A, 1B:
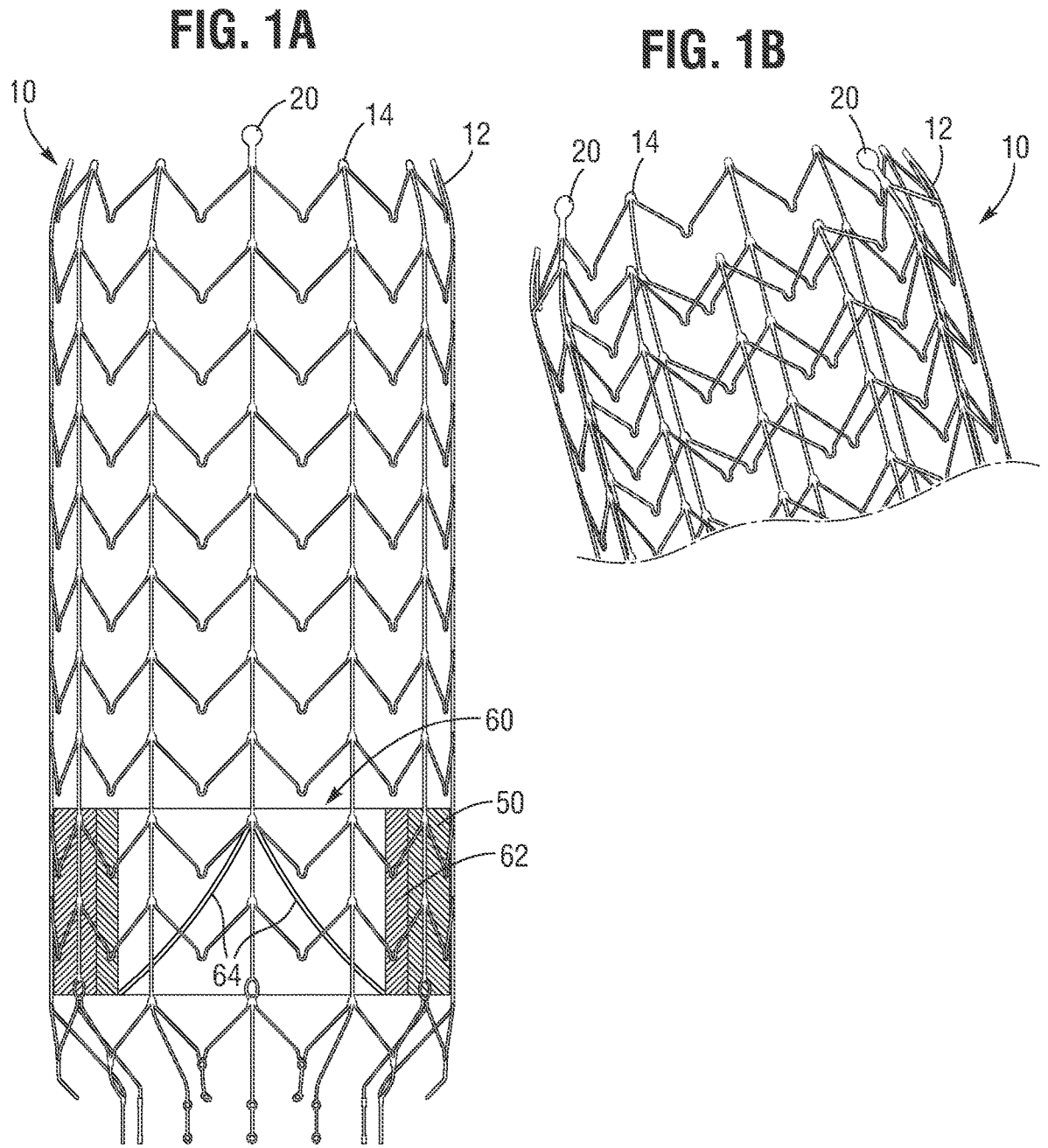
FIG. 1A is a side elevation view of a frame, according to one embodiment.
FIG. 1B is a closeup view of a proximal end portion of the frame of FIG. 1A.

FIGS. 1-2 show an implantable frame 10, according to one example embodiment. The frame 10 includes a plurality of struts 12 interconnected to each other to form a mesh structure which can be radially expandable and compressible. Thus, the frame 10 can be crimped to a compressed state and percutaneously introduced in the compressed state on a delivery catheter, and then expanded to a radially expanded state once the frame reaches the implantation site.

As described more fully below, the delivery catheter can have a frame retaining mechanism that is configured to allow controlled and precise deployment of the frame 10 from a retaining sheath so as to minimize or prevent jumping of the frame 10 from the sheath. The delivery catheter can also be configured to allow partial expansion of the frame 10 outside the retaining sheath at the implantation site, and then recapture the frame 10 back into the retaining sheath if needed, as further described below.

As shown in FIGS. 1-2, the frame 10 can have at least one extension members, or connecting post, 20 extending from a proximal end 14 of the frame 10. The connecting post 20 forms a releasable connection with the retaining mechanism of a delivery apparatus, as further described below. In some embodiments, the frame 10 can have a plurality of connecting posts 20 that are circumferentially disposed at the proximal end 14 of the frame. In some embodiments, the plurality of connecting posts 20 can be spaced apart from each other uniformly at the proximal end 14 of the frame. In other embodiments, the plurality of connecting posts 20 can be spaced apart from each other non-uniformly. In the depicted embodiment, two connecting posts 20 are positioned diametrically opposed at the proximal end 14 of the frame. In other embodiments, the frame 10 can have any number of connecting posts 20.

Although the connecting posts 20 (and 120, 220 described below) are shown to extend from the proximal end of the frame, it should be understood that the connecting posts 20

(and 120, 220) can also extend from a distal end of the frame, or from any portion of the frame that is between the proximal and distal ends, and the same principles described herein apply.

The frame 10 can be formed using any suitable technique. Suitable techniques include, for example, laser cutting the frame from a tube of material and optionally shape setting the laser-cut frame to its desired shape if it is formed from a shape memory material, such as Nitinol.

The frame can be made from a highly flexible metal, metal alloy, or polymer. Examples of metals and metal alloys that can be used include, but are not limited to, Nitinol and other shape memory alloys, but other metals and highly resilient or compliant non-metal materials can also be used to make the frame. When made of shape-memory materials, the frame 10 can be compressed to a small size for delivery into a patient, and then when the compression force is released, the frame 10 can self-expand back to its pre-compressed, functional size. Alternatively, the frame 10 can be made from plastically-expandable materials, such as a cobalt-chromium alloy and stainless steel. When made of plastically-expandable materials, the frame can be radially compressed for delivery into a patient and radially expanded to its functional size with an expansion device, such as an inflatable balloon.

In the illustrated embodiment, the frame 10 is configured as a docking station or a docking device for receiving another transcatheter device, such as a transcatheter prosthetic valve 60. The frame 10, when expanded, can be configured or shaped to conform to an interior shape of a portion of the vasculature in which it is to be implanted. The docking device can include one or more sealing members (not shown), which can be made of fabric, polymer, or other covering and are attached to a portion of the frame 10. The sealing members can be configured to contact an interior surface of the circulatory system at the implantation site so as to inhibit or prevent paravalvular leakage.

The docking device can also optionally include one or more valve seats 50 configured to receive and support the transcatheter prosthetic valve 60 after the docking device is implanted in the circulatory system. The one or more valve seats 50 can be attached to the frame 10 or integrally formed with the frame 10. In addition, the docking device can include one or more retaining members (not shown), which can be any structure that sets the position of the docking device in the circulatory system. For example, the retaining members can press against or into the inside surface or contour/extend around anatomical structures of the circulatory system to set and maintain the position of the docking station. In some embodiments, the retaining members can be part of or define a portion of the frame 10 and/or sealing portion of the docking device. In some embodiments, the retaining members can be a separate component that is attached to the frame 10 of the docking device.

The illustrated docking device and prosthetic valve 60 are particularly suited to be deployed in the inferior vena cava (IVC). However, the docking device and prosthetic valve 60 can be deployed in any interior surface within the heart or a lumen of the body. For example, the various docking devices and valves described herein can be deployed in the superior vena cava (SVC), the tricuspid valve (TV), the pulmonary valve (PV), pulmonary artery (PA), the mitral valve (MV), the aortic valve (AV), aorta, or other vasculature/lumens in the body. Further details regarding the docking station and methods for implanting the docking station are disclosed in U.S. Patent Publications Nos. 2019/0000615 and 2017/0231756, which are incorporated herein by reference.

The prosthetic valve 60 can include a frame 62 and one or more prosthetic leaflets 64 configured to regulate the flow of blood through the valve in one direction. Further details of the prosthetic valve are disclosed in U.S. Publication Nos. 2018/0028310 and 2012/0123529 and WIPO Publication No. 2018/222799, which are incorporated herein by reference.

FIGS. 2A-2C show a connecting post 120 of a frame (e.g., frame 10) (the mesh structure of the frame is omitted for clarity), and a retainer 150 configured to receive the connecting post 120, according to one embodiment. The retainer 150 can be a component of a delivery catheter, as described more fully below.

The connecting post 120 can have an elongated arm 122 (or "body portion") and an enlarged head (or "head portion") 124 affixed to a proximal end of the arm 122. In the depicted embodiment, the head 124 has a generally round disc-shape, and the diameter of the head 124 is greater than the width of the arm 122. As described herein, the width of the arm 122 is measured in a direction that is substantially perpendicular to the axial axis of the arm 122.

As shown, the retainer 150 can have a generally cylindrical shape, although the retainer can take a variety of different forms. The retainer 150 has a proximal end 152, a distal end 154, and a central lumen 156 extending between the proximal end 152 and the distal end 154. As described below, the central lumen 156 can be so configured to allow an inner shaft of a delivery catheter to extend through thereof.

The retainer 150 includes at least one post connector region 160 disposed on its circumference or outer surface 158 and configured to receive the connecting post 120. For example, the post connector region 160 can include a slot 162 and a recess 164 connected to the slot 162. The slot 162 can be configured to receive at least a proximal portion 126 of the arm 122 of the connecting post 120, and the recess 164 can be configured to receive the head 124 of the connecting post 120.

As shown, the slot 162 can extend from the distal end 154 of the retainer 150 to the recess 164. The axial length of the slot 162 can be configured to be a predefined percentage (e.g., 30%, 20%, 10%, etc.) of the axial length of the arm 122 of the connecting post 120. The proximal portion 126 of the arm 122 can have a width that is about the same as or slightly smaller than the width of the slot 162 so that the proximal portion 126 of the arm 122 can snugly fit into the slot 162. In some embodiments, the width of the slot 162 can range from about 0.8 mm to about 1.0 mm. In some embodiments, the width of the slot 162 can be about 0.9 mm.

The recess 164 can be defined by a floor 166, a distal wall 168, a proximal wall 170 and two side boundaries 172 where the floor 166 intersects the cylindrical outer surface 158 of the retainer. The slot 162 can bisect the distal wall 168 from the middle and divide it into two equal parts. The slot 162 can be substantially perpendicular to the distal wall 168. In some embodiments, the intersection of the slot 162 and the distal wall 168 can form a rounded corner or fillet 174 with a predefined arc angle.

When the head 124 is disposed at the most distal position within the recess 164 (as shown in FIGS. 2A-2B), a distal edge portion 128 of the head 124 can contact the fillet 174 and form a fillet interface area 130 (as shown in FIG. 2C). Thus, when recapturing a partially expanded frame into a sheath or capsule as described more fully below, the expansion force of the frame causes the head 124 of the connecting post 120 to press against the retainer 150 at the fillet interface area 130.

The arc angle of the fillet 174 can be configured to achieve a predefined arc length of the fillet interface area 130. For example, the arc length of the fillet interface area 130 can range from about 0.05 mm to about 0.15 mm. In some embodiments, the arc length of the fillet interface area 130 can be about 0.1 mm.

The floor 166 can have a generally rectangular shape, although in some embodiments the floor 166 can take a variety of other shapes. The area of the floor 166 can be substantially larger than an area of the head 124 of the connecting post 120. Thus, when the head 124 is disposed at the most distal position within the recess 164 (as shown in FIGS. 2A-2B), any part of the head 124 other than the fillet interface area 130 can be spaced apart from any wall (e.g., 168, 170) or boundary 172 of the recess 164. Thus, when the arm 122 slides axially within the slot 162, the head 124 can also move axially within the recess 164, limited by the distal wall 168 and the proximal wall 170.

The floor 166 can be substantially flat, although in some embodiments the floor 166 can be curved (e.g., having a concave or convex surface). The disc-shaped head 124 can have a top surface 132 and a bottom surface 134. The top surface 132 can be substantially flat or curved. The bottom surface 134 can also be substantially flat or curved. In an example embodiment, both the bottom surface 134 and the floor 166 are substantially flat. The distance between the top surface 132 and the bottom surface 134 defines a thickness of the head 124. In some embodiments, the thickness of the head 124 is about the same or smaller than a depth of the distal wall 168 of the recess 164. In some embodiments, the thickness of the head 124 is slightly larger than (e.g., by a predefined percentage) a depth of the distal wall 168 of the recess 164. As disclosed herein, a depth of the recess 164 can be defined by the depth of the distal wall 168.

The arm 122 can have a top surface that is generally coplanar with the top surface 132 of the head 124, and a bottom surface that is generally coplanar with the bottom surface 134 of the head 124. The distance between the top and bottom surfaces of the arm 122 can define a thickness of the arm 122. In some embodiments, the thickness of the arm 122 is about the same or smaller than a depth of the slot 162 (measured in a radial direction that is normal to the floor 166). In some embodiments, the thickness of the arm 122 is slightly larger than (e.g., by a predefined percentage) a depth of the slot 162.

In some embodiments, the retainer 150 can have a plurality of post connector regions 160 configured to receive a plurality of connecting posts 120. For example, when the frame has two connecting posts 120 located on diametrically opposite sides at the proximal end of the frame, the retainer 150 can be configured to have two post connector regions 160 located on circumferentially opposite sides of the retainer 150, each being configured to receive a corresponding connecting post 120 of the frame.

FIGS. 3A-3C show the connecting post 120 received by another retainer 180, according to one embodiment. Similar to the retainer 150 described above, the retainer 180 has at least one post connector region 181 disposed on its circumference and configured to receive the connecting post 120. Similarly, the post connector region 181 includes a slot 182 and a recess 184 connected to the slot 182. The slot 182 can be configured to receive at least a proximal portion 126 of the arm 122 of the connecting post 120, and the recess 184 can be configured to receive the head 124 of the connecting post 120.

The post connector region 181 is similar to the post connector region 160 shown in FIGS. 2A-2C, except for the width of the slot 182 and the arc angle of the fillet 186. Specifically, the slot 182 can be configured to be slightly wider than the slot 162 and the arc angle of the fillet 186 can be larger than that of the fillet 174.

For example, in some embodiments, the width of the slot 182 can range from about 0.9 mm to about 1.1 mm. In some embodiments, the width of the slot 182 can be about 1 mm. Likewise, when the head 124 is disposed at the most distal position within the recess 184 (as shown in FIGS. 3A-3B), a distal edge portion 128 of the head 124 can contact the fillet 186 and form a fillet interface area 188 (as shown in FIG. 3C). Increasing the arc angle of the fillet 186 can lead to a larger fillet interface area 188. In some embodiments, the arc length of the fillet interface area 188 can range from about 0.2 mm to about 0.4 mm. In some embodiments, the arc length of the fillet interface area 188 can be about 0.3 mm. Increasing the arc length of the fillet interface area 188 can reduce the pressure generated thereof when the connecting post 120 is pressed (under an applied force) against the retainer 180 at the fillet interface area 188.

FIG. 4A shows a connecting post 220 of a frame (e.g., frame 10), according to an alternative embodiment. FIGS. 4B-4D show the connecting post 220 being received by the retainer 150, although it should be understood that the connecting post 220 can also be received by the retainer 180 or other variants of the retainer 150.

Like the connecting post 120, the connecting post 220 has an elongated arm 222 and an enlarged head 224 affixed to a proximal end of the arm 222. The arm 222 can bisect a distal edge 228 of the head 224 from the middle and divide it into two parts that are symmetric relative to a longitudinal axis of the arm 222. In other embodiments, the arm 222 can bisect the distal edge 228 into two parts that are asymmetric about the longitudinal axis of the arm 222.

The connecting post 220 is generally similar to the connecting post 120 except for the shape of the head 224. For example, unlike the connecting post 120 which has a disc-shaped head 124, the head 224 has a wedge shape which tapers from a distal edge 228 to a proximal edge 236 of the head 224. In addition, the head 224 can have two opposing curved sides 238 bulging outwardly relative to the proximal edge 236 and the distal edge 228. The curved sides 238 can define a width (D) of the head 224, which is the largest distance between the two opposing curved sides 238 along a direction that is substantially perpendicular to the arm 222.

The distal edge 228 can have a substantially flat portion 240 that is substantially perpendicular to the arm 222, and the substantially flat portion 240 can have a predefined length (L). In the depicted embodiment, the distal edge 228 has two substantially flat portions 240 that are symmetrically positioned on opposite sides of the arm 222. Thus, the total length of the substantially flat portions 240 can be 2 L. In other embodiments, the two substantially flat portions 240 that are asymmetrically positioned on opposite sides of the arm 222.

In some embodiments, the length (L) of a substantially flat portion 240 can be configured to be a predefined percentage of the width (D) of the head 224. For example, in some embodiments, the ratio L/D can range from about 10% to about 40%. In some embodiments, the ratio L/D can range from about 20% to about 30%.

In some embodiments, the length (L) of a substantially flat portion 240 and the width of the arm 222 (W) can be configured to have a predefined ratio. For example, in some embodiments, the ratio L/D can range from about 0.2 to about 1.0. In some embodiments, the ratio L/D can range from about 0.4 to about 0.6.

The distal wall 168 of the recess 164 on the retainer 150 can have a substantially flat portion 169 that is configured to interface with each substantially flat portion 240 on the distal edge 228 of the head 224 of the connecting post 220. Specifically, when the head 224 is disposed at the most distal position within the recess 164 (as shown in FIGS. 4B-4D), the substantially flat portions 240 on the connecting post 220 can abut against the substantially flat portion 169 of the distal wall 168 on the retainer 150.

Thus, when recapturing a partially expanded frame into a sheath or capsule as described more fully below, the head 224 of the connecting post 220 can press against the retainer 150 at the interface formed between the substantially flat portions 240, 169.

Optionally, as shown in FIGS. 4A-4D, the distal edge 228 of the head 224 can have a recessed portion 242 connecting each substantially flat portion 240 of the distal edge 228 and the proximal end of the arm 222. Each recessed portion 242 can extend proximally relative to the substantially flat portion 240, and the depth of the recess portion 242 can be predefined. Thus, when the substantially flat portions 240 on the connecting post 220 abuts against the substantially flat portion 169 of the distal wall 168, each recessed portion 242 can avoid contact with the fillet 174 (formed between the slot 162 and the distal wall 168), therefore not interfering with proper abutment between the substantially flat portions 240, 169.

The wedge-shaped connecting post head 224 can have certain advantages compared to the disk-shaped connecting post head 124, which is configured to press against the retainer 150 (or 180) at the fillet interface area 130 (or 188). For example, the fillet 174 (or 186) is rounded, rather than perpendicular to the slot 162 (or 182). Further, the arc length of the fillet 174 (or 186) can be limited to a relatively small dimension due to the constraint of the corresponding arc angle. Thus, the force applied by the connecting post head 124 on the fillet interface area 130 (or 188) can create uneven pressure and develop high stress on the fillet 174 (or 186), which may result in corrosion and material deformation at the fillet interface area 130 (or 188), thereby potentially interfering with proper disengagement of the connecting post 120 from the retainer 150 (or 180). In contrast, the connecting post head 224 and the retainer 150 can form an abutment between the substantially flat portions 240, 169, which are substantially perpendicular to the slot 162. Further, the length (L) of the substantially flat portion 240 can be configured to be much larger than the arc length of the fillet interface area 130 (or 188). Thus, the pressure generated at the substantially flat portions 240, 169 can be more evenly distributed (i.e., mitigating the risk of generating concentrated stress at the interface region), thereby reducing the risk of corrosion or material deformation of the connecting post 220 and/or the retainer 150. Such material deformation can cause the connecting post to "sink" into the retainer material, thereby increasing the risk of fault detachment of the implant from the delivery apparatus (the implant not detaching from the delivery apparatus). By more evenly distributing the pressure and reducing concentrated stress, softer material (e.g., polymers) can be used for designing the connecting post and/or the retainer, thus reducing the cost of manufacturing such components without increasing the risk of corrosion.

Like the connecting post 120, the connecting post 220 can be configured such that when the head 224 is disposed at the most distal position within the recess 164 (as shown in FIGS. 3B-3C), any part of the head 224 other than the substantially flat portion 240 can be spaced apart from any wall (e.g., 168, 170) or boundary 172 of the recess 164.

Similarly, the top surface 232 of the head 224 can be substantially flat or curved, and the bottom surface 234 of the head can also be substantially flat or curved. In some embodiments, the thickness of the head 224 is about the same or smaller than a depth of the distal wall 168 of the recess 164. In some embodiments, the thickness of the head 224 is slightly larger than (e.g., by a predefined percentage) a depth of the distal wall 168 of the recess 164.

Figures 5A, 5B, 5C:
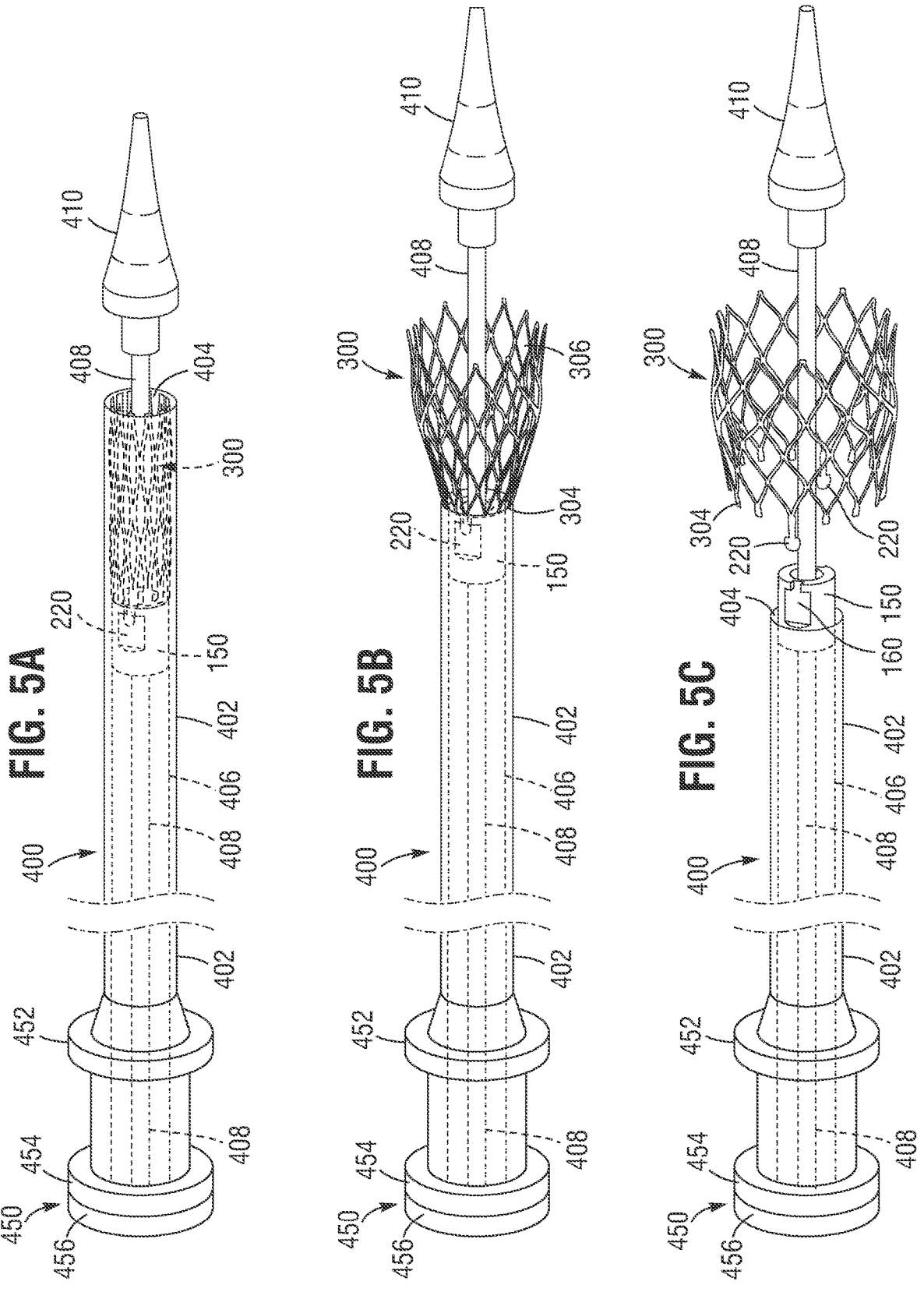
FIG. 5A is a side perspective view of a delivery apparatus and a frame crimped in a compressed state within an outer sheath of the delivery apparatus, according to one embodiment.
FIG. 5B is a side perspective view of the delivery apparatus and the frame depicted in FIG. 5A, wherein a distal portion of the frame is expanded outside of, and a proximal portion of the frame remains compressed within the outer sheath.
FIG. 5C is a side perspective view of the delivery apparatus and the frame depicted in FIG. 5A, wherein the frame is fully expanded outside of the outer sheath.

FIGS. 5A-5C show the deployment of an expandable frame 300 using an exemplary delivery device or delivery apparatus 400, according to one embodiment. In the depicted embodiment, the frame 300 has two wedge-shaped connecting posts 220 extending from a proximal end of the frame 300. In other embodiments, the number of connecting posts 220 can be one or greater than two. In alternative embodiments, the frame 300 can have one or more disk-shaped connecting posts 120, and it should be understood that the same principles on frame deployment described below apply.

In particular embodiments, the frame 300 is a frame of a prosthetic, transcatheter heart valve. The prosthetic heart valve can have valve structure, such as a plurality of prosthetic leaflets, mounted inside of the frame 300 for regulating the flow of blood through the frame in one direction. Further details of the prosthetic heart valve are disclosed in U.S. Publication No. 2014/0343670 and 2016/0317301, which are incorporated herein by reference. It should be noted that the delivery device 400 also can be used to deliver a docking device, such as the frame 10, to a location within a patient's vasculature.

As shown in FIG. 5A, the delivery device 400 includes an outer sheath 402 which can be configured to retain the frame 300 in a compressed state inside a lumen 404 of the outer sheath 402. The compressed frame 300 can be connected to a retainer 150 (or 180) retained inside the lumen 404 and positioned proximal to the frame 300. Specifically, the connecting posts 220 of the frame 300 can be connected to the retainer 150 via the post connector region 160 as described above.

The delivery catheter 400 can include a first shaft 406 extending through the lumen 404 of the outer sheath 402. The first shaft 406 can be configured to be axially moveable relative to the outer sheath 402. A distal end of the first shaft 406 can be connected to a proximal end of the retainer 150 such that axial movement of the first shaft 406 can cause corresponding axial movement of the retainer 150 relative to the outer sheath 402.

The delivery device 400 can also include a second shaft 408 (or "inner shaft") extending through a central lumen of the first shaft 406, the lumen 156 of the retainer 150, and an interior space of the frame 300. A distal end of the second shaft 408 can be connected to a nose cone 410, which can reduce resistance and facilitate advancement of the delivery catheter 400 through the patient's vasculature. In certain embodiments, a guide wire (not shown) can extend through a central lumen of the second shaft 408 and an inner lumen of the nose cone 410 so that the delivery device 400 can be advanced over the guide wire through the patient's vasculature.

As shown in FIG. 5B, the delivery device 400 can be configured to move at least a distal portion 306 of the frame 300 out of the outer sheath 402 while retaining the connecting post 220 of the frame 300 and the retainer 150 connected thereto within the outer sheath 402.

Uncovered by the outer sheath 402, the exposed distal portion 306 of the frame 300 can self-expand in the radial direction. However, because the connecting post 220 of the frame 300 is still connected to the post connector region 160 of the retainer 150, which is retained within the outer sheath 402, a proximal end 304 of the frame 300 and any proximal portion of the frame 300 still covered by the outer sheath 402 remain radially compressed. In this state, the frame 300 is in a partially expanded state.

In some embodiments, the partially expanded frame 300 can be recaptured or pulled back into the outer sheath 402. Specifically, by moving the first shaft 406 in a proximal direction relative to the outer sheath 402, the retainer 150 can also be moved proximally, thus pulling the connected frame 300 in the proximal direction. As a result, the uncovered distal portion 306 of the frame 300 can be retracted back into the lumen 404, causing the frame 300 to return to the compressed state. The capability of recapturing the frame 300 back into the outer sheath 402 can be helpful if the initial placement of the frame 300 is incorrect, imperfect, or if the operator wants to abort or redo the procedure for any reason.

When recapturing the partially expanded frame 300 into the outer sheath 402, a force is generated between the interface of the connecting post 220 and the retainer 150. Specifically, the substantially flat portion 240 on the connecting post 220 can press against the substantially flat portion 169 of the distal wall 168 on the retainer 150. As noted above, the substantially flat surfaces 240, 169 allow even distribution of the pressure on the abutment interface, thereby reducing the risk of corrosion or material deformation of the connecting post 220 and/or the retainer 150.

As shown in FIG. 5C, the delivery device 400 can be configured to move the connecting post 220 of the frame 60 out of the outer sheath 402. Unrestrained by the outer sheath 402, the connecting post 220 can detach from the retainer 150 under the resiliency of the frame, thereby allowing the frame 300 to self-expand to a fully expanded state. After expanding the frame 300 in the desired location, the delivery device can be removed from the patient's body. If being used to implant a docking frame (e.g., frame 10), the delivery device 400 (or a separate delivery device 400) can be used to deliver and implant a prosthetic heart valve within the docking frame.

The delivery device 400 can further include a handle mechanism 450 which can be maneuvered by the operator to advance or retract the delivery device 400 through a patient's vasculature. In some embodiments, the handle mechanism 450 can be connected to proximal ends of the outer sheath 402, the first shaft 406, and the second shaft 408.

The handle mechanism 450 can be configured to move the retainer 150 axially relative to the outer sheath 402. In some embodiments, the handle mechanism 450 can include a plurality of knobs (or buttons or other actuating mechanisms) that can be actuated by the operator to control different components of the delivery catheter 30. For example, the proximal end of the outer sheath 402 can be operatively coupled to a first knob 452, the proximal end of the first shaft 406 can be operatively coupled to a second knob 454, and the proximal end the second shaft 408 can be operatively coupled to a third knob 456.

In some embodiments, operation (e.g., rotational or axial movement) of the first knob 452 can cause the outer sheath 402 to slide over and retain the frame 30 or withdraw proximally so as to expose and release the frame 300. In some embodiments, operation of the first knob 452 can cause rotational movement of the outer sheath 402 relative to the first and second shafts 406, 408.

In some embodiments, operation (e.g., rotational or axial movement) of the second knob 454 can cause the first shaft 406 to rotate within and/or slide along the lumen 404 of the outer sheath 402. Because the distal end of the first shaft 406 is connected to the retainer 150, operation of the second knob 454 can produce limited rotational and/or axial movement of the retainer 150 relative to the outer sheath 402.

Thus, by operating the first knob 452 and/or the second knob 454, the retainer 150 can be moved axially relative to the outer sheath 402. Depending on the direction and/or extent of the movement of the retainer 150, the frame 300 connected thereof can be partially moved out of the outer sheath 402, retracted back into the lumen 404, or fully pushed out of the outer sheath 402.

In some embodiments, operation (e.g., rotational or axial movement) of the third knob 456 can cause the second shaft 408 (and the nose cone 410 connected thereto) to slide longitudinally relative to the first shaft 406 and the outer sheath 402. For example, in certain embodiments, the second shaft 408 can be moved distally to move the nose cone 410 distally relative to the outer sheath 402 when deploying the frame 300.

Further details of the construction of the handle with knobs and the means for operating the handle and knobs are described in U.S. Patent Application Publication Nos. 2013/0030519, 2009/0281619, 2008/0065011, and 2007/0005131. Alternatively, different components of the delivery catheter can be controlled by different forms of actuation mechanism other than knobs, such as push buttons, joysticks, voice-controlled actuators, etc.

As introduced above with reference to FIGS. 5A-5C, a nose cone 410 can form a distal end of the delivery apparatus 400. During assembly of the delivery apparatus 400 (or another, similar delivery apparatus for a prosthetic medical device), a stylet comprising an elongate shaft can be inserted through an inner lumen or bore of the nose cone of the delivery apparatus to protect the nose cone during assembly, packaging, and handling of the delivery apparatus prior to insertion into a patient. The shaft of the stylet can also extend through the guidewire lumen of the inner shaft of the delivery apparatus 400. For example, the stylet can protect the components through which it passes from being degraded or deformed, such as by compressive and/or bending forces experienced by the components of the delivery apparatus (e.g., the nose cone) during assembly and packaging of the delivery apparatus, and during subsequent handling of the delivery apparatus prior to an implantation procedure.

As an exemplary embodiment, referring to FIGS. 6-10, a removable stylet 500 can be inserted through an apex (or distal end formed by the apex) 502 of a nose cone 504 of a delivery apparatus. As described herein, the nose cone 504 can be the nose cone 410 described above or another nose cone configured to facilitate advancement of the delivery apparatus through the patient's vasculature. The delivery apparatus can be the delivery apparatus 400 shown in FIGS. 5A-5C or another delivery apparatus for a prosthetic medical device. The stylet 500 can be inserted along and through an axial bore (or lumen) 506 extending through the nose cone 504, as shown in FIGS. 6-9 (described further below). In some embodiments, the stylet 500 can comprise a relatively rigid material, such as a metal or plastic.

In some embodiments, the nose cone 504 can comprise a body 508 that tapers (in width or diameter) from a first (proximal) end portion 510 of the body 508 to a second (distal) end portion 512 of the body 508 which can define the apex 502 at a distal end of the body 508 (FIGS. 6-9).

Figure 6:
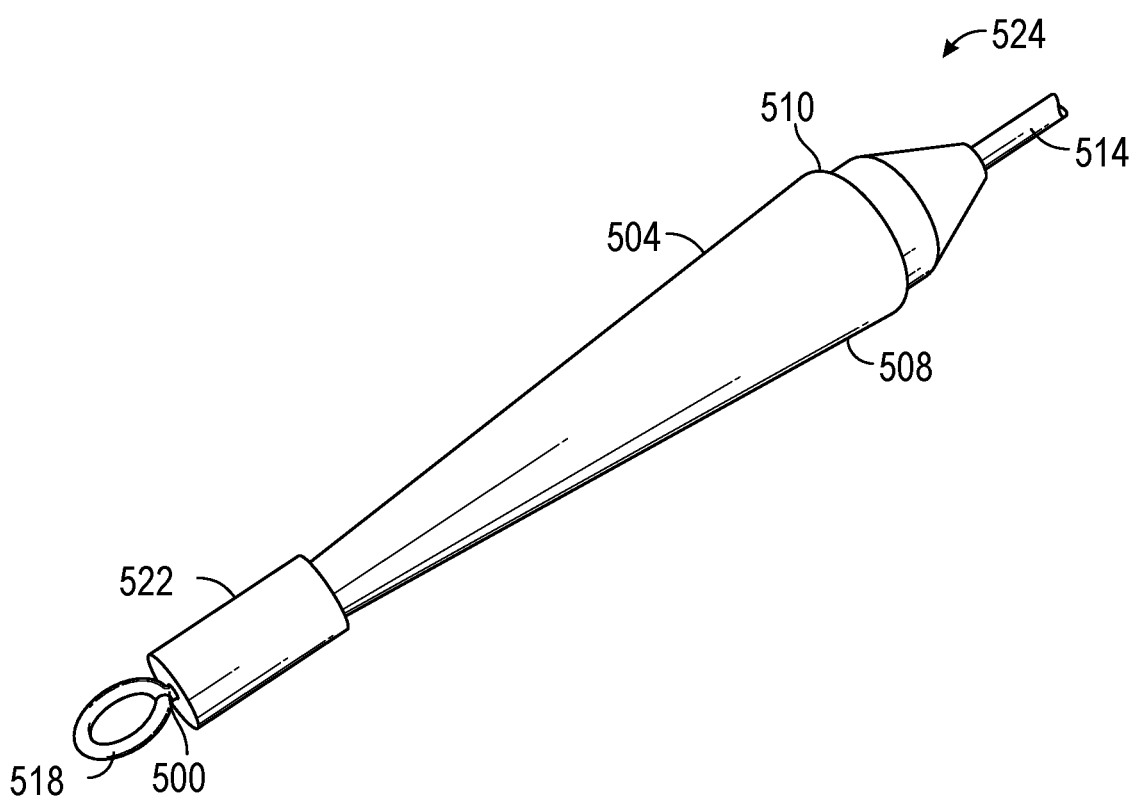
FIG. 6 is a perspective view of a system including a delivery apparatus with a nose cone at its distal end, a stylet extending through an axial bore of the nose cone, and an exemplary embodiment of a spacer positioned between an end portion of the stylet and an apex of the nose cone, the spacer shown covering the apex and offsetting the end portion of the stylet from the apex of the nose cone.
Figure 7:
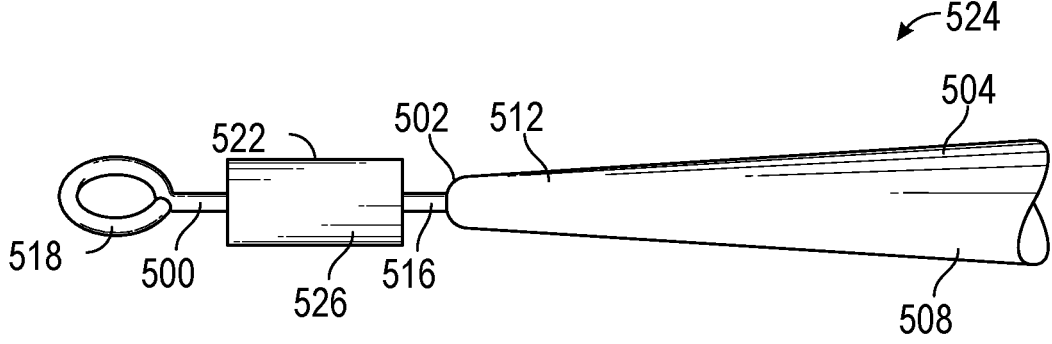
FIG. 7 is a side view of the system of FIG. 6 showing the spacer disposed between, in an axial direction, the end portion of the stylet and the apex of the nose cone, the spacer shown spaced away from each of the nose cone and the end portion of the stylet.
Figure 8:
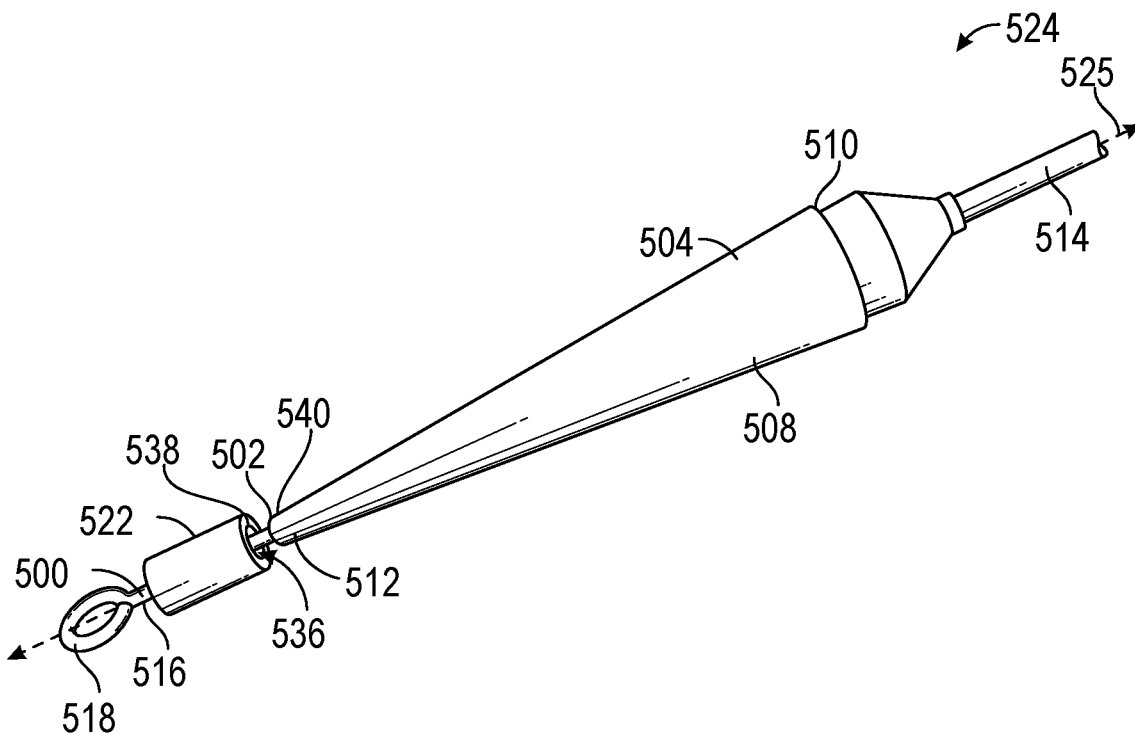
FIG. 8 is a perspective view of the configuration of the system shown in FIG. 7, with the spacer spaced away from the nose cone.
Figure 9:
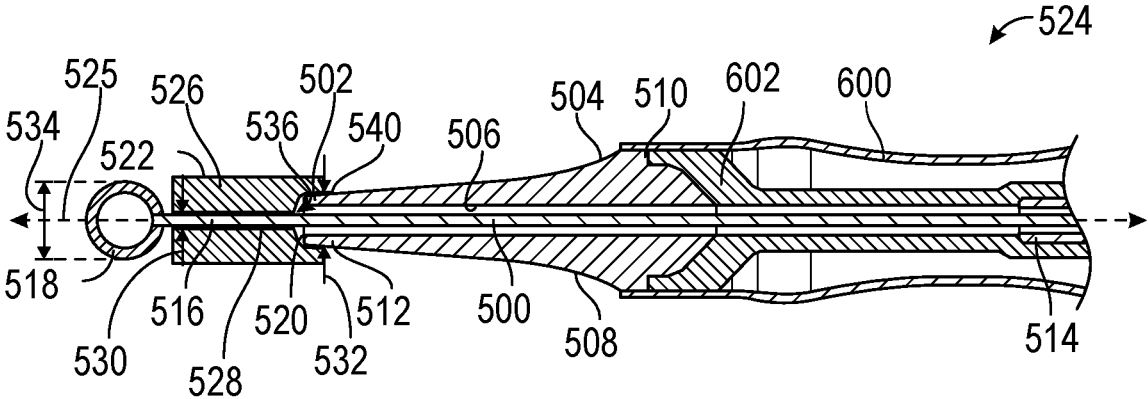
FIG. 9 is a cross-sectional side view of the spacer of FIG. 6, covering a portion of a nose cone of a delivery apparatus and arranged between the nose cone and an end portion of a stylet.

In some embodiments, the nose cone 504 can be connected to a shaft 514 of the delivery apparatus that extends proximally from the proximal end portion 510 of the body 508 (FIGS. 6 and 8). The shaft 514 can be the inner shaft of the delivery apparatus, such as inner shaft 408. Further, in some embodiments, the proximal end portion 510 of the body 508 can taper from a widest portion of the proximal end portion 510 to the shaft 514, in a proximal direction (FIGS. 6 and 8). It should be noted that FIGS. 6-8 show one embodiment of the nose cone 504 which includes the shaft 514 and can be used in a first delivery apparatus and FIG. 9 shows another embodiment of the nose cone 504 (not including the shaft 514) which is configured to be used with a delivery apparatus for a balloon expandable prosthetic medical device.

The stylet 500 can comprise an elongate shaft 516 and an end portion 518 disposed at a distal end of the shaft 516.

In some embodiments, the shaft 516 of the stylet 500 can extend through the axial bore 506 of the nose cone 504 which can extend through the body 508 and the shaft 514.

In some embodiments, as shown in FIGS. 6-9, the end portion 518 of the stylet 500 can be configured as an open loop (or eyelet).

In other embodiments, instead of a circular loop, the end portion 518 of the stylet 500 can comprise a differently shaped element (e.g., square, oval, or the like) that is wider than a diameter of the shaft 516 and an opening 520 of the axial bore 506 of the nose cone 504 at the apex 502 (FIG. 9). For example, the end portion 518 of the stylet 500 can be open (have a central opening) configured to receive a pin and restrict axial movement of the stylet 500 (e.g., into the axial bore 506).

In some cases, compressive forces applied by the end portion 518 of the stylet 500 on the apex 502 of the nose cone 504 (which can comprise a relatively soft material that is softer than the stylet 500) can result in degradation and/or deformation of the apex 502 during packaging, shipping, storage, and/or handling of the delivery apparatus prior to use. This deformation can result in a non-smooth and/or step-like transition between the more rigid guidewire (used during an implantation procedure, as described herein) and the nose cone 504, which can result in abrasion against a delivery sheath through with the delivery apparatus is advanced and/or the patient's vasculature.

FIGS. 6-9 show an embodiment of a spacer 522 for a system 524 including a delivery apparatus with the nose cone 504 at its distal end and the stylet 500, the spacer 522 configured to be positioned between and offset the end portion 518 of the stylet 500 and the apex 502 of the nose cone 504 from each other. As a result, the end portion 518 is prevented from contacting the apex 502 of the nose cone 504 when the shaft 516 of the stylet 500 is arranged within the axial bore 506 of the nose cone 504.

The system 524 can include packaging that encloses and houses the delivery apparatus and the stylet 500 during shipping and storage of the delivery apparatus. For example, the packaging can include a sealed flexible pouch or package that encloses the delivery apparatus and the stylet and maintains a sterile environment for the delivery apparatus. The packaging can further include a box containing the flexible pouch (with the delivery apparatus). Prior to use in an operating room, the delivery apparatus can be removed from the packaging and the stylet 500 can be removed from the delivery apparatus and discarded.

The spacer 522 can be configured as an annular cylinder or tube, as shown in FIGS. 6-9. However, in other embodiments, the spacer 522 can be configured (shaped) as a bead (sphere), cube, ellipsoid, or another offsetting member that can offset the end portion 518 of the stylet 500 from the apex 502 of the nose cone 504.

The spacer 522 can have a length, in an axial direction relative to a central longitudinal axis 525 of the system 524 (FIGS. 8 and 9), that is configured to offset the end portion 518 of the stylet 500 from the apex 502 of the nose cone 504 such that the end portion 518 of the stylet 500 does not contact the apex 502 of the nose cone 504.

The spacer 522 can comprise a body 526 defining an inner bore (or channel) 528 (FIG. 9). The inner bore 528 can have a first diameter 530 at a first end (e.g., distal end) of inner bore 528 and a second diameter 532 at an opposite, second end (e.g., proximal end) of the inner bore 528 of the spacer 522. The first end can face and be disposed adjacent to the end portion 518 of the stylet while the second end can face and be disposed adjacent to the apex 502 of the nose cone.

The first diameter 530 can be configured to be smaller than a diameter (outer diameter) or width 534 of the end portion 518 of the stylet. As a result, the end portion 518 is maintained outside the spacer 522 and is prevented from passing through the inner bore 528 of the spacer 522. Further, the first diameter 530 can be slightly larger than a diameter of the shaft 516 of the stylet 500 in order to accommodate the shaft 516 and allow the shaft 516 to slide axially within the inner bore 528.

In some embodiments, the second diameter 532 can be the same as the first diameter 530.

As shown in FIG. 9, in some embodiments, the second diameter 532 can be larger than the first diameter 530. For example, the second diameter 532 can be larger (e.g., slightly larger) than a diameter of the apex 502 of the nose cone. Further, the inner bore 528 can comprise a cavity 536 at the second end of the spacer 522 with an opening 538 to the cavity 536 having the second diameter 532 (FIGS. 8 and 9). The cavity 536 can extend from the second end of the spacer 522 into a portion of the body 526 of the spacer 522 (FIG. 9). The cavity 536 can be shaped to receive the apex 502 of the nose cone. For example, when the apex 502 is received within the cavity 536, inner walls of the body 526, defined by the cavity 536, surround an outer surface 540 of the apex 502 (as shown in FIGS. 6 and 9), thereby preventing another component from pressing against the apex 502. In this way, by covering (and enclosing) the apex 502 of the nose cone 504 by the second (proximal) end of the spacer 522, the apex 502 can be protected from additional compressive or bending forces.

Figure 10:
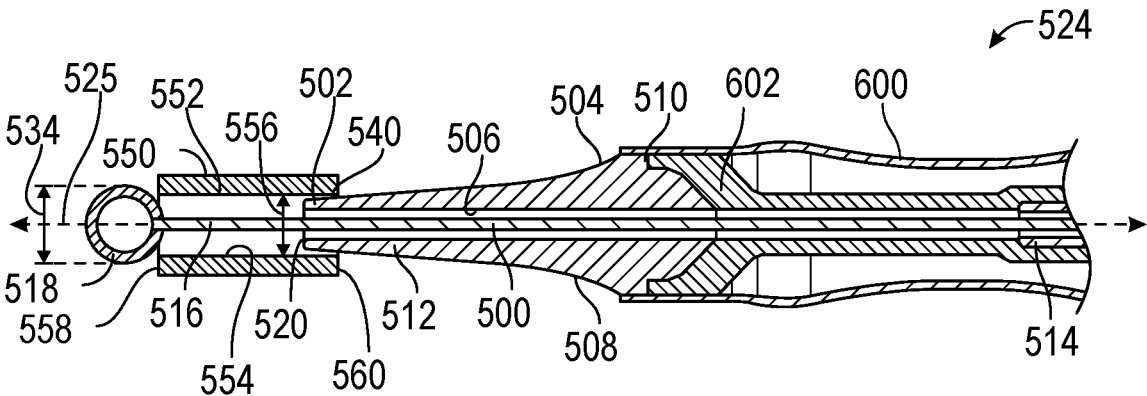
FIG. 10 is a cross-sectional side view of another embodiment of a spacer arranged between an end portion of a stylet and an apex of a nose cone of a delivery apparatus, the spacer shown covering the apex and offsetting the end portion of the stylet from the apex of the nose cone.

FIG. 10 shows an embodiment of a spacer 550 for the system 524. Similar to the spacer 522 of FIGS. 6-9, the spacer 550 is configured to be positioned between and offset the end portion 518 of the stylet 500 and the apex 502 of the nose cone 504 from each other. As a result, the end portion 518 is prevented from contacting the apex 502 of the nose cone 504 when the shaft 516 of the stylet 500 is arranged within the axial bore 506 of the nose cone 504.

The spacer 550 comprises a body 552 defining an inner bore (or channel) 554. The inner bore 554 can have a constant diameter 556. For example, the diameter 556 of the inner bore 554 can be constant from a first end (e.g., distal end) 558 of the inner bore 554 of the spacer 550 to a second end (e.g., proximal end) 560 of the inner bore 554 of the spacer 550.

The diameter 556 can be smaller than the diameter (outer diameter) or width 534 of the end portion 518 of the stylet 500 but larger than a diameter or width of the apex 502 of the nose cone 504. As such, as shown in FIG. 10, the second end 560 of the spacer 550 can fit over and around an end portion of the nose cone 504, including the apex 502.

FIGS. 6-8 show the distal end portion of a delivery apparatus, such as delivery apparatus 400, which can be used for delivering and implanting a self-expandable medical implant, such as implant 10 or 300, or a self-expandable prosthetic valve or a mechanically expandable prosthetic valve. Examples of self-expandable prosthetic valves and delivery apparatuses therefor are disclosed in U.S. Pat. Nos. 8,652,202 and 9,155,619 and U.S. Publication No. 2014/0343670, which are incorporated herein by reference. Examples of mechanically expandable prosthetic valves and delivery apparatuses therefor are disclosed in U.S. Publication Nos. 2018/0153689, 2018/0311039, 2019/0060057, PCT Application No. PCT/US2021/022467, filed Mar. 16, 2021, and U.S. Application Nos. 63/085,947, filed Sep. 30, 2020, 63/138,599, filed Jan. 18, 2021, and 63/179,766, filed Apr. 26, 2021, which are incorporated herein by reference.

FIGS. 9-10 show the distal end portion of a delivery apparatus that can be used for delivering and implanting balloon-expandable implants, such as a balloon-expandable prosthetic valve. The delivery apparatus in FIGS. 9-10 can include an inflatable balloon 600 for radially expanding the implant within a patient's body. The balloon 600 can be secured at its distal end to the nose cone 504 and/or a shoulder or stop member 602 disposed within the balloon 600, which assists in retaining the implant on the balloon. The inner shaft 514 of the delivery apparatus can be connected to a proximal end of the shoulder 602. Examples of balloon-expandable prosthetic valves and delivery apparatuses therefor are disclosed in U.S. Pat. No. 9,393,110, U.S. Publication Nos. 2013/0030519, 2018/0028310 and 2019/0365530, and U.S. Application No. 63/138,890, filed Jan. 19, 2021, which are incorporated herein by reference.

Either spacer 522, 550 can be used in the packaging for delivery apparatuses for self-expandable implants (such as shown in FIGS. 6-8) or for delivery apparatuses for balloon-expandable implants (such as shown in FIGS. 9-10).

General Considerations

It should be understood that the disclosed embodiments can be adapted to deliver and implant prosthetic devices in any of the native annuluses of the heart (e.g., the pulmonary, mitral, and tricuspid annuluses), and can be used with any of various delivery approaches (e.g., retrograde, antegrade, transseptal, transventricular, transatrial, etc.).

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "connected" generally mean electrically, electromagnetically, and/or physically (e.g., mechanically or chemically) coupled or linked and does not exclude the presence of intermediate elements between the coupled or associated items absent specific contrary language.

As used herein, a surface (e.g., a wall or a portion of an object) is deemed to be "substantially perpendicular" to an axis or another surface if the angle therebetween ranges from about 85 degrees to about 95 degrees.

As used herein, a surface is deemed to be "substantially flat" if the surface's flatness tolerance, which is defined as the minimum distance separating two parallel planes between which the surface can be contained, is smaller than 1 mm, or the ratio between the surface's flatness tolerance to the length of the surface is smaller than 0.1.

As used herein, the term "approximately" and "about" means the listed value and any value that is within 20% of the listed value. For example, "about 1 mm" means any value between about 0.8 mm and about 1.2 mm, inclusive.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

Directions and other relative references (e.g., inner, outer, top, bottom, etc.) may be used to facilitate discussion of the drawings and principles herein, but are not intended to be limiting. For example, certain terms may be used such as "inside," "outside,", "upper," "lower," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, a "top" part can become a "bottom" part simply by turning the object over. Nevertheless, it is still the same part and the object remains the same. As used herein, "and/or" means "and" or "or", as well as "and" and "or".

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. An implantable frame comprising: a plurality of struts interconnected to each other to form a mesh structure, the mesh structure being radially expandable and compressible; and a connecting post extending from an end of the mesh structure, the connecting post comprising a body portion and a head portion affixed to an end of the body portion; wherein the head portion has a first edge extending outwardly of the body portion, wherein the first edge comprises a substantially flat portion that is substantially perpendicular to the body portion.

Example 2. The frame of any example herein, particularly example 1, wherein the plurality of struts comprise a self-expandable material.

Example 3. The frame of any example herein, particularly any one of examples 1-2, wherein the head portion has a wedge shape which tapers from the first edge to a second edge of the head portion, the second edge being farther away from the body portion relative to the first edge.

Example 4. The frame of any example herein, particularly example 3, wherein the head portion of the connecting post has a curved side connecting the first edge and the second edge, the curved side bulging outwardly relative to the first and second edges.

Example 5. The frame of any example herein, particularly any one of examples 1-4, wherein the first edge is divided by the body portion into two halves, and the substantially flat portion is divided by the body portion into two halves.

Example 6. The frame of any example herein, particularly example 5, wherein both the two halves of the first edge and the two halves of the substantially flat portion are symmetric about the body portion.

Example 7. The frame of any example herein, particularly any one of examples 1-6, wherein the head portion of the connecting post has a first surface configured to interface with a floor of a recess located on a retainer, wherein the first surface and the floor are substantially flat.

Example 8. The frame of any example herein, particularly example 7, wherein the head portion of the connecting post has a second surface opposite the first surface, the second surface being substantially flat, wherein the first and second surfaces define a thickness of the head portion of the connecting post, the thickness being equal to or smaller than a depth of the recess.

Example 9. The frame of any example herein, particularly any one of examples 1-8, wherein the first edge of the head portion has a recessed portion connecting between the substantially flat portion of the first edge and the end of the body portion, wherein the recessed portion of the first edge extends inwardly into the head portion.

Example 10. The frame of any example herein, particularly any one of examples 1-9, wherein a length of the substantially flat portion of the first edge is a predefined percentage of a width of the head portion.

Example 11. The frame of any example herein, particularly example 10, wherein a length of the substantially flat portion of the first edge and a width of the body portion has a predefined ratio.

Example 12. The frame of any example herein, particularly any one of examples 1-11, wherein the connecting post is one of a plurality of connecting posts that are circumferentially disposed at the end of the frame.

Example 13. The frame of any example herein, particularly example 12, wherein the plurality of connecting posts are spaced apart from each other uniformly at the end of the frame.

Example 14. The frame of any example herein, particularly any one of examples 1-13, wherein the end of the frame is a proximal end of the frame.

Example 15. An assembly comprising: a radially expandable and compressible frame comprising a plurality of struts interconnected to each other to form a mesh structure and a connecting post extending from an end of the mesh structure; and a delivery device comprising a retainer configured to be releasably connected to the connecting post; wherein the connecting post comprises a body portion and a head portion affixed to an end of the body portion; wherein the head portion has a first edge extending outwardly of the body portion, wherein the first edge comprises a substantially flat portion that is substantially perpendicular to the body portion.

Example 16. The assembly of any example herein, particularly example 15, wherein the plurality of struts comprise a self-expandable material.

Example 17. The assembly of any example herein, particularly any one of examples 15-16, wherein the first end of the frame is a proximal end of the frame.

Example 18. The assembly of any example herein, particularly any one of examples 15-17, wherein the head portion has a wedge shape which tapers from the first edge to a second edge of the head portion, the second edge being farther away from the body portion relative to the first edge.

Example 19. The assembly of any example herein, particularly example 18, wherein the head portion of the connecting post has a curved side connecting the first edge and the second edge, the curved side bulging outwardly relative to the first and second edges.

Example 20. The assembly of any example herein, particularly any one of examples 15-19, wherein the first edge is divided by the body portion into two halves that are symmetric about the body portion, and the substantially flat portion is divided by the body portion into two halves that are symmetric about the body portion.

Example 21. The assembly of any example herein, particularly any one of examples 15-20, wherein the first edge of the head portion has a recessed portion connecting between the substantially flat portion of the first edge and the end of the body portion, wherein the recessed portion of the first edge extends inwardly into the head portion.

Example 22. The assembly of any example herein, particularly any one of examples 15-21, wherein a length of the substantially flat portion of the first edge is a predefined percentage of a width of the head portion.

Example 23. The assembly of any example herein, particularly any one of examples 15-21, wherein a length of the substantially flat portion of the first edge and a width of the body portion has a predefined ratio.

Example 24. The assembly of any example herein, particularly any one of examples 15-23, wherein the retainer has a generally cylindrical shape.

Example 25. The assembly of any example herein, particularly any one of examples 15-24, wherein the retainer comprises a post connector region, wherein the post connector region comprises a slot and a recess connected to the slot, wherein the slot is configured to receive at least an end portion of the body portion of the connecting post, and the recess is configured to receive the head portion of the connecting post.

Example 26. The assembly of any example herein, particularly example 25, wherein the slot and the recess are located on a circumference of the retainer.

Example 27. The assembly of any example herein, particularly any one of examples 25-26, wherein the recess comprises a floor and a first wall, wherein the first wall is substantially perpendicular to an axial axis of the slot.

Example 28. The assembly of any example herein, particularly example 27, wherein the first wall is connected to an end of the slot via a fillet having a predefined arc angle.

Example 29. The assembly of any example herein, particularly any one of examples 27-28, wherein the head portion of the connecting post has a first surface configured to interface with the floor of the recess on the retainer, wherein the first surface and the floor are substantially flat.

Example 30. The assembly of any example herein, particularly example 29, wherein the head portion of the connecting post has a second surface opposite the first surface, the second surface being substantially flat, wherein the first and second surfaces define a thickness of the head portion of the connecting post, the thickness being equal to or smaller than a depth of the first wall of the recess.

Example 31. The assembly of any example herein, particularly any one of examples 27-30, wherein the first wall of the recess has a substantially flat portion that is configured to interface with the substantially flat portion on the first edge of the head portion of the connecting post.

Example 32. The assembly of any example herein, particularly any one of examples 27-31, wherein the recess is sized such that when the first edge of the head portion of the connecting post contacts the first wall of the recess, any part of the head portion other than the first edge is spaced apart from any other wall or boundary of the recess.

Example 33. The assembly of any example herein, particularly any one of examples 15-32, wherein the retainer comprises a central lumen.

Example 34. The assembly of any example herein, particularly any one of examples 15-33, wherein the connecting post is one of a plurality of connecting posts that are circumferentially disposed at the end of the frame, wherein the plurality of connecting posts are configured to be releasably connected to respective post connector regions of the retainer.

Example 35. The assembly of any example herein, particularly example 34, wherein the plurality of connecting posts are spaced apart from each other uniformly at the end of the frame.

Example 36. The assembly of any example herein, particularly any one of examples 15-35, wherein the delivery device comprises an outer sheath configured to retain the frame in a compressed state inside a lumen of the outer sheath, wherein the connecting post of the frame is connected to the retainer that is retained inside the lumen.

Example 37. The assembly of any example herein, particularly example 36, wherein the delivery device comprises a shaft extending through the lumen of the outer sheath, wherein the shaft is axially moveable relative to the outer sheath.

Example 38. The assembly of any example herein, particularly example 37, wherein an end of the shaft is connected to the retainer such that axial movement of the shaft causes axial movement of the retainer relative to the outer sheath.

Example 39. The assembly of any example herein, particularly any one of examples 36-38, wherein the delivery device is configured to move at least a portion of the frame out of the outer sheath while retaining the connecting post of the frame and the retainer connected thereto within the outer sheath.

Example 40. The assembly of any example herein, particularly example 39, wherein the delivery catheter is configured to recapture the portion of the frame back into the lumen.

Example 41. The assembly of any example herein, particularly any one of examples 36-40, wherein the delivery catheter is configured to move the connecting post of the frame out of the outer sheath such that the connecting post can detach from the retainer and the frame can expand to an expanded state.

Example 42. The assembly of any example herein, particularly any one of examples 36-41, further comprises a handle mechanism configured to move the retainer axially relative to the outer sheath.

Example 43. The assembly of any example herein, particularly any one of examples 15-42, wherein the frame further comprises a valve seat configured to support an expandable prosthetic valve.

Example 44. An assembly comprising: a radially expandable and compressible frame comprising a plurality of struts interconnected to each other to form a mesh structure and a connecting post coupled to the frame; and a delivery catheter configured to deliver the frame to a target implantation site, the delivery catheter comprising a retainer configured to be releasably connected to the connecting post; wherein the connecting post and the retainer are configured to form a contacting interface that is substantially perpendicular to an axial axis of the delivery catheter when the connecting post is connected to the retainer.

Example 45. The assembly of any example herein, particularly example 44, wherein the delivery catheter comprises an outer sheath configured to retain the frame in a compressed state inside a lumen of the outer sheath, wherein the connecting post of the frame is connected to the retainer that is retained inside the lumen.

Example 46. The assembly of any example herein, particularly example 45, wherein the delivery catheter comprises a shaft extending through the lumen of the outer sheath, wherein the shaft is axially moveable relative to the outer sheath.

Example 47. The assembly of any example herein, particularly example 46, wherein an end of the shaft is connected to the retainer such that axial movement of the shaft causes axial movement of the retainer relative to the outer sheath.

Example 48. The assembly of any example herein, particularly any one of examples 45-47, wherein the delivery catheter is configured to move at least a portion of the frame out of the outer sheath while retaining the connecting post of the frame and the retainer connected thereto within the outer sheath.

Example 49. The assembly of any example herein, particularly example 48, wherein the delivery catheter is configured to recapture the portion of the frame back into the lumen.

Example 50. The assembly of any example herein, particularly any one of examples 45-49, wherein the delivery catheter is configured to move the connecting post of the frame out of the outer sheath such that the connecting post can detach from the retainer and the frame can expand to an expanded state.

Example 51. The assembly of any example herein, particularly any one of examples 45-50, further comprises a handle mechanism configured to move the retainer axially relative to the outer sheath.

Example 52. The assembly of any example herein, particularly any one of examples 44-51, wherein the plurality of struts comprise a self-expandable material.

Example 53. The assembly of any example herein, particularly any one of examples 44-52, wherein the connecting post comprises a body portion and a head portion affixed to an end of the body portion.

Example 54. The assembly of any example herein, particularly example 53, wherein the head portion has a first edge extending outwardly of the body portion, wherein the first edge comprises a substantially flat portion that is substantially perpendicular to the body portion, wherein the substantially flat portion is a part of the contact interface when the connecting post is connected to the retainer.

Example 55. The assembly of any example herein, particularly example 54, wherein the head portion has a wedge shape which tapers from the first edge to a second edge of the head portion, the second edge being farther away from the body portion relative to the first edge.

Example 56. The assembly of any example herein, particularly example 55, wherein the head portion of the connecting post has a curved side connecting the first edge and the second edge, the curved side bulging outwardly relative to the first and second edges.

Example 57. The assembly of any example herein, particularly any one of examples 54-56, wherein the first edge is divided by the body portion into two halves that are symmetric about the body portion, and the substantially flat portion is divided by the body portion into two halves that are symmetric about the body portion.

Example 58. The assembly of any example herein, particularly any one of examples 54-57, wherein the first edge of the head portion has a recessed portion connecting between the substantially flat portion of the first edge and the end of the body portion, wherein the recessed portion of the first edge extends inwardly into the head portion.

Example 59. The assembly of any example herein, particularly any one of examples 54-58, wherein a length of the substantially flat portion of the first edge is a predefined percentage of a width of the head portion.

Example 60. The assembly of any example herein, particularly any one of examples 54-58, wherein a length of the substantially flat portion of the first edge and a width of the body portion has a predefined ratio.

Example 61. The assembly of any example herein, particularly any one of examples 44-60, wherein the retainer has a generally cylindrical shape.

Example 62. The assembly of any example herein, particularly any one of examples 53-61, wherein the retainer comprises a post connector region, wherein the post connector region comprises a slot and a recess connected to the slot, wherein the slot is configured to receive at least an end portion of the body portion of the connecting post, and the recess is configured to receive the head portion of the connecting post.

Example 63. The assembly of any example herein, particularly example 62, wherein the slot and the recess are located on a circumference of the retainer.

Example 64. The assembly of any example herein, particularly any one of examples 62-63, wherein the recess comprises a floor and a first wall, wherein the first wall is substantially perpendicular to an axial axis of the slot.

Example 65. The assembly of any example herein, particularly example 64, wherein the first wall is connected to an end of the slot via a fillet having a predefined arc angle.

Example 66. The assembly of any example herein, particularly any one of examples 64-65, wherein the head portion of the connecting post has a first surface configured to interface with the floor of the recess on the retainer, wherein the first surface and the floor are substantially flat.

Example 67. The assembly of any example herein, particularly example 66, wherein the head portion of the connecting post has a second surface opposite the first surface, the second surface being substantially flat, wherein the first and second surfaces define a thickness of the head portion of the connecting post, the thickness being equal to or smaller than a depth of the first wall of the recess.

Example 68. The assembly of any example herein, particularly any one of examples 64-67, wherein the first wall of the recess has a substantially flat portion that is a part of the contact interface when the connecting post is connected to the retainer.

Example 69. The assembly of any example herein, particularly any one of examples 64-68, wherein the recess is sized such that when the first edge of the head portion of the connecting post contacts the first wall of the recess, any part of the head portion other than the first edge is spaced apart from any other wall or boundary of the recess.

Example 70. The assembly of any example herein, particularly any one of examples 44-69, wherein the retainer comprises a central lumen.

Example 71. The assembly of any example herein, particularly any one of examples 44-70, wherein the connecting post is one of a plurality of connecting posts that are circumferentially disposed at a proximal end of the frame, wherein the plurality of connecting posts are configured to be releasably connected to respective post connector regions of the retainer.

Example 72. The assembly of any example herein, particularly example 71, wherein the plurality of connecting posts are spaced apart from each other uniformly at the proximal end of the frame.

Example 73. The assembly of any example herein, particularly any one of examples 44-72, further comprises a prosthetic valve configured to be secured within the frame.

Example 74. A method for deploying a self-expandable frame, the method comprising: retaining the frame in a compressed state within an outer sheath, wherein a connecting post of the frame is attached to a retainer retained within the outer sheath such that a substantially flat portion of the connecting post abuts against a substantially flat portion of the retainer, wherein the substantially flat portion of the connecting post and the substantially flat portion of the retainer are substantially perpendicular to an axial axis of the frame.

Example 75. The method of any example herein, particularly example 74, further comprising moving the frame in a first direction relative to the outer sheath such that at least a portion of the frame is uncovered by the outer sheath and self-expands while retaining the connecting post of the frame and the retainer connected thereto within the outer sheath.

Example 76. The method of any example herein, particularly example 75, wherein the portion of the frame being uncovered by the outer sheath is a distal portion of the frame.

Example 77. The method of any example herein, particularly any one of examples 75-76, further comprising moving the frame in a second direction relative to the outer sheath so as to recapture the portion of the frame back into the outer sheath, wherein the second direction is opposite to the first direction.

Example 78. The method of any example herein, particularly any one of examples 75-77, further comprising detaching the connecting post from the retainer so as to allow the frame to expand to an expanded state.

Example 79. The method of any example herein, particularly example 78, wherein detaching the connecting post form the retainer comprises moving the frame in the first direction relative to the outer sheath such that the connecting post is uncovered by the outer sheath.

Example 80. The method of any example herein, particularly any one of examples 75-79, wherein moving the frame relative to the outer sheath comprises actuating a handle mechanism connected to the outer sheath.

Example 81. The method of any example herein, particularly example 80, wherein actuating the handle mechanism comprises moving an inner shaft axially relative to the outer sheath, wherein the inner shaft extend through a lumen of the outer sheath and is connected to the retainer.

Example 82. The method of any example herein, particularly any one of examples 74-81, wherein the connecting post comprises a body portion and a head portion affixed to an end of the body portion, and wherein the substantially flat portion of the connecting post is located at a first edge of the head portion, wherein the first edge extends outwardly of the body portion.

Example 83. The method of any example herein, particularly example 82, wherein the retainer comprises a post connector region, wherein the post connector region comprises a slot and a recess connected to the slot, wherein the slot is configured to receive at least an end portion of the body portion of the connecting post, and the recess is configured to receive the head portion of the connecting post.

Example 84. The method of any example herein, particularly example 83, wherein the substantially flat portion of the retainer is located at a wall of the recess, the wall extending outwardly of the slot.

Example 85. A system comprising: a delivery apparatus comprising: a handle portion; a first shaft extending distally from the handle portion; and a nose cone mounted to a distal end portion of the first shaft; a stylet comprising a shaft and an end portion that is wider than a diameter of the shaft, the shaft extending though an opening in an apex of the nose cone and through an axial bore of the nose cone; and a spacer disposed around the shaft of the stylet and between the apex of the nose cone and the end portion of the stylet.

Example 86. The system of any example herein, particularly example 85, wherein the nose cone is tapered from a wider, proximal end of the nose cone to the apex, the apex disposed at a distal end of the nose cone.

Example 87. The system of any example herein, particularly example 85 or example 86, wherein the spacer comprises a body defining an inner bore of the spacer that is configured to receive the shaft of the stylet, the inner bore having a first diameter at a distal end of the spacer that is greater than the diameter of the shaft of the stylet and less than a diameter or width of the end portion of the stylet.

Example 88. The system of any example herein, particularly example 87, wherein the first diameter is constant along a length of the inner bore, from the distal end to a proximal end of the spacer and wherein the first diameter is larger than a diameter of the apex of the nose cone.

Example 89. The system of any example herein, particularly example 87, wherein the inner bore of the spacer has a second diameter at a proximal end of the spacer that is larger than the first diameter.

Example 90. The system of any example herein, particularly example 89, wherein the second diameter is configured to receive the apex of the nose cone therethrough and wherein the proximal end of the spacer includes a cavity that extends into the body of the spacer, toward the distal end, and is configured to receive the apex of the nose cone.

Example 91. The system of any example herein, particularly any one of examples 85-90, wherein the end portion of the stylet is configured as a loop.

Example 92. The system of any example herein, particularly any one of examples 85-91, wherein the spacer is an annular cylinder.

Example 93. The system of any example herein, particularly any one of examples 85-92, wherein the spacer has a length, in an axial direction, that is configured to offset the end portion of the stylet from the apex of the nose cone such that the end portion of the stylet does not contact the apex of the nose cone.

Example 94. The system of any example herein, particularly any one of examples 85-93, wherein the delivery apparatus further comprises: a rotatable second shaft, the first shaft extending through and distal to a distal end of the second shaft; and an inflatable balloon including a proximal end portion coupled to the second shaft and a distal end portion coupled to the nose cone.

Example 95. The system of any example herein, particularly example 94, wherein the balloon overlays a valve mounting portion of the delivery apparatus that is configured to receive a prosthetic valve in a radially compressed state.

Example 96. An assembly comprising: a nose cone forming a distal end of a delivery apparatus for a prosthetic medical device, the nose cone comprising a tapered body that narrows to an apex at a distal end of the nose cone and an axial bore extending through a center of the tapered body; a stylet comprising a shaft extending through the axial bore of the nose cone and an end portion that is wider than the shaft and disposed outside and distal to the apex of the nose cone; and a spacer disposed around the shaft of the stylet, distal to the apex, and configured to offset the end portion of the stylet from the apex.

Example 97. The assembly of any example herein, particularly example 96, wherein the spacer is disposed between, in an axial direction, the apex and the end portion of the stylet.

Example 98. The assembly of any example herein, particularly example 96 or example 97, wherein the spacer comprises a cavity at a proximal end of the spacer configured to receive the apex such that the spacer surrounds an outer surface of the apex.

Example 99. The assembly of any example herein, particularly example 98, wherein the spacer comprises a body defining an inner bore configured to receive the shaft of the stylet, the inner bore having a diameter at a distal end of the spacer that is smaller than a diameter or width of the end portion of the stylet, and wherein the inner bore widens to the cavity at a location that is closer to the proximal end than the distal end of the spacer.

Example 100. The assembly of any example herein, particularly example 96 or example 97, wherein the spacer comprises a body defining an inner bore configured to receive the shaft of the stylet and the apex of the nose cone, the inner bore having a diameter that is smaller than a diameter or width of the end portion of the stylet and larger than a diameter of the apex of the nose cone.

Example 101. The assembly of any example herein, particularly any one of examples 95-100, wherein the nose cone is coupled to a distal end of a shaft of the delivery apparatus, the shaft extending from a handle portion of the delivery apparatus.

Example 102. The assembly of any example herein, particularly any one of examples 95-101, wherein the end portion of the stylet is configured as a loop having a diameter that is wider than a diameter of the axial bore of the nose cone.

Example 103. The assembly of any example herein, particularly any one of examples 95-102, wherein the nose cone comprises a softer material than the stylet.

Exemplary Alternatives

In view of the many possible examples to which the principles of the disclosed technology may be applied, it should be recognized that the described examples are only illustrative should not be taken as limiting the scope of the disclosure. Rather, the scope of the claimed subject matter is defined by the following claims and their equivalents.

The invention claimed is:

1. An implantable frame comprising:
   a plurality of struts interconnected to each other to form a mesh structure, the mesh structure being radially expandable and compressible; and
   a connecting post extending from an end of the mesh structure, the connecting post comprising a body portion and a head portion affixed to an end of the body portion;
   wherein the head portion has a first edge extending outwardly of the body portion, wherein the first edge comprises a substantially flat portion that is substantially perpendicular to the body portion,
   wherein the first edge of the head portion has a recessed portion connecting between the substantially flat portion of the first edge and the end of the body portion, wherein the recessed portion of the first edge extends inwardly into the head portion.

2. The frame of claim 1, wherein the plurality of struts comprises a self-expandable material.

3. The frame of claim 1, wherein the head portion has a wedge shape which tapers from the first edge to a second edge of the head portion, the second edge being farther away from the body portion relative to the first edge.

4. The frame of claim 3, wherein the head portion of the connecting post has a curved side connecting the first edge and the second edge, the curved side bulging outwardly relative to the first and second edges.

5. The frame of claim 1, wherein the first edge is divided by the body portion into two halves.

6. The frame of claim 5, wherein both the two halves of the first edge are symmetric about the body portion.

7. The frame of claim 1, wherein the head portion of the connecting post has a first surface configured to interface with a floor of a recess located on a retainer, wherein the first surface and the floor are substantially flat.

8. The frame of claim 7, wherein the head portion of the connecting post has a second surface opposite the first surface, the second surface being substantially flat, wherein the first and second surfaces define a thickness of the head portion of the connecting post, the thickness being equal to or smaller than a depth of the recess.

9. The frame of claim 1, wherein a length of the substantially flat portion of the first edge is a predefined percentage of a width of the head portion.

10. The frame of claim 9, wherein a length of the substantially flat portion of the first edge and a width of the body portion has a predefined ratio.

11. The frame of claim 1, wherein the connecting post is one of a plurality of connecting posts that are circumferentially disposed at the end of the frame.

12. The frame of claim 11, wherein the plurality of connecting posts are spaced apart from each other uniformly at the end of the frame.

13. The frame of claim 1, wherein the end of the frame is a proximal end of the frame.

14. An assembly comprising:
   a radially expandable and compressible frame comprising a plurality of struts interconnected to each other to form a mesh structure and a connecting post extending from an end of the mesh structure; and
   a delivery device comprising a retainer configured to be releasably connected to the connecting post;
   wherein the connecting post comprises a body portion and a head portion affixed to an end of the body portion;
   wherein the head portion has a first edge extending outwardly of the body portion, wherein the first edge comprises a substantially flat portion that is substantially perpendicular to the body portion,
   wherein the retainer comprises a post connector region, wherein the post connector region comprises a recess configured to receive the head portion of the connecting post, wherein the recess comprises a first end wall, a second wall, and a floor having two side edges extending axially from the first end wall to the second end wall, wherein the head portion has a maximum width measured in a direction perpendicular to a length of the connecting post and the floor has a width extending from one side edge of the floor to the other side edge of the floor, wherein the width of the floor is greater than the maximum width of the head portion, and the head portion is spaced from the side edges of the floor along an axis that is perpendicular to the length of the connecting post when the head portion is disposed in the recess.

15. The assembly of claim 14, wherein the post connector region further comprises a slot connected to the recess, wherein the slot is configured to receive at least an end portion of the body portion of the connecting post.

16. The assembly of claim 14, wherein the retainer comprises a central lumen.

17. The assembly of claim 14, wherein the connecting post is one of a plurality of connecting posts that are circumferentially disposed at the end of the frame, wherein the plurality of connecting posts are configured to be releasably connected to respective post connector regions of the retainer.

18. The assembly of claim 14, wherein the delivery device comprises an outer sheath configured to retain the frame in a compressed state inside a lumen of the outer sheath, wherein the connecting post of the frame is connected to the retainer that is retained inside the lumen.

19. An assembly comprising:

a radially expandable and compressible frame comprising a plurality of struts interconnected to each other to form a mesh structure and a connecting post coupled to the frame; and a delivery catheter configured to deliver the frame to a target implantation site, the delivery catheter comprising a retainer configured to be releasably connected to the connecting post;

wherein the connecting post and the retainer are configured to form a contacting interface that is substantially perpendicular to an axial axis of the delivery catheter when the connecting post is connected to the retainer, wherein the retainer comprises a recess configured to receive a head portion of the connecting post, wherein the recess comprises a rectangular, flat floor having two axially extending side edges that intersect a cylindrical outer surface of the retainer.

20. The assembly of claim 14, wherein the floor is flat and the side edges of the floor of the recess intersect a cylindrical outer surface of the retainer.

21. The assembly of claim 20, wherein the post connector region further comprises a slot configured to receive the body portion of the connecting post, wherein the head portion comprises a bottom surface, a top surface, and an outer peripheral side edge extending from the bottom surface to the top surface, wherein the outer peripheral side edge contacts the first end wall of the recess at two locations on opposing sides of and adjacent the slot and is spaced from the second end wall of the recess and the two side edges of the floor.

* * * * *